United States Patent
Yamasaki et al.

(10) Patent No.: US 6,638,427 B2
(45) Date of Patent: Oct. 28, 2003

(54) WASTE WATER TREATMENT METHOD BEING ABLE TO TREAT SURFACE ACTIVE AGENT, NITROGEN, HYDROGEN PEROXIDE AND PHOSPHOR WITH HIGH EFFICIENCY

(75) Inventors: Kazuyuki Yamasaki, Hiroshima (JP); Noriyuki Tanaka, Fukuyama (JP); Shigeki Matsumoto, Fukuyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 42 days.

(21) Appl. No.: 10/087,763

(22) Filed: Mar. 5, 2002

(65) Prior Publication Data

US 2002/0100718 A1 Aug. 1, 2002

Related U.S. Application Data

(62) Division of application No. 09/432,599, filed on Nov. 3, 1999, now Pat. No. 6,375,837.

(30) Foreign Application Priority Data

Nov. 10, 1998 (JP) .......................................... 10-319082

(51) Int. Cl.[7] ................................................. C02F 3/00
(52) U.S. Cl. ........................ 210/605; 210/630; 210/616
(58) Field of Search ............................... 210/630, 605, 210/615–617, 623–628

(56) References Cited

U.S. PATENT DOCUMENTS

| | | | |
|---|---|---|---|
| 5,081,954 A | 1/1992 | Monus | |
| 5,578,214 A | * 11/1996 | Yamasaki et al. | ............ 210/650 |
| 5,618,428 A | 4/1997 | Oslund | |
| 5,849,194 A | 12/1998 | Yamasaki et al. | |
| 6,177,005 B1 | 1/2001 | Yamasaki | |

FOREIGN PATENT DOCUMENTS

| | | |
|---|---|---|
| JP | A-5-4090 | 1/1993 |
| JP | A-6-343974 | 12/1994 |
| JP | A-7-136667 | 5/1995 |
| JP | A-8-197070 | 8/1996 |
| JP | A-9-174081 | 7/1997 |
| JP | A-10-5769 | 1/1998 |
| JP | A-8-57498 | 12/1998 |

OTHER PUBLICATIONS

U.S. patent application Ser. No. 09/432,599 filed Nov. 3, 1999 (Parent Case).

* cited by examiner

Primary Examiner—Chester T. Barry
(74) Attorney, Agent, or Firm—Nixon & Vanderhye P.C.

(57) ABSTRACT

A waste water treatment equipment treats a fluorine waste water containing organic matter, nitrogen, phosphor and hydrogen peroxide by an anaerobic tank 3 in which a calcium carbonate mineral 9 is placed and an aerobic tank 15 in which the calcium carbonate mineral 9 is placed and into which a biologically treated water is introduced from a treatment equipment 444 of another system. Therefore, the fluorine in the waste water can be treated by the calcium carbonate mineral 9 placed in the anaerobic tank 3 and the aerobic tank 15 with the formation of calcium fluoride 11. The organic matter of the surface active agent and so on in the waste water can be treated by the microorganism included in the biologically treated water. Furthermore, nitrate nitrogen can be treated so as to be reduced to a nitrogen gas in the anaerobic tank 3, while ammoniacal nitrogen and nitrite nitrogen can be treated so as to be oxidized in the aerobic tank 15. That is, the waste water treatment equipment can highly efficiently treat the surface active agent, nitrogen, polychlorinated aluminum, macromolecular coagulant, hydrogen peroxide and phosphor in the waste water, by which the waste can be reduced.

8 Claims, 20 Drawing Sheets

Fig. 2A

WHEN FLUORINE WASTE WATER CONTAINING SURFACE ACTIVE AGENT, NITROGEN, PHOSPHOR AND HYDROGEN PEROXIDE HAS NORMAL CONCENTRATION

| TANK NAME | RETENTION TIME | TIMING (ELAPSED TIME) 1:00 2:00 3:00 4:00 5:00 6:00 7:00 8:00 9:00 10:00 11:00 12:00 13:00 14:00 15:00 |
|---|---|---|
| 1ST WATER TANK | 1HR. | |
| 2ND WATER TANK (ANAEROBIC TANK) | 2HR. | |
| 3RD WATER TANK (AEROBIC TANK) | 2HR. | |
| 4TH WATER TANK | 20MIN. | |
| 5TH WATER TANK | 20MIN. | |
| 6TH WATER TANK | 20MIN. | |
| 7TH WATER TANK (SEDIMENTATION TANK) | 3HR. | |
| 8TH WATER TANK (CONDENSATION TANK) | 5HR. | |

WHEN FLUORINE WASTE WATER CONTAINING SURFACE ACTIVE AGENT, NITROGEN, PHOSPHOR AND HYDROGEN PEROXIDE HAS LOW CONCENTRATION

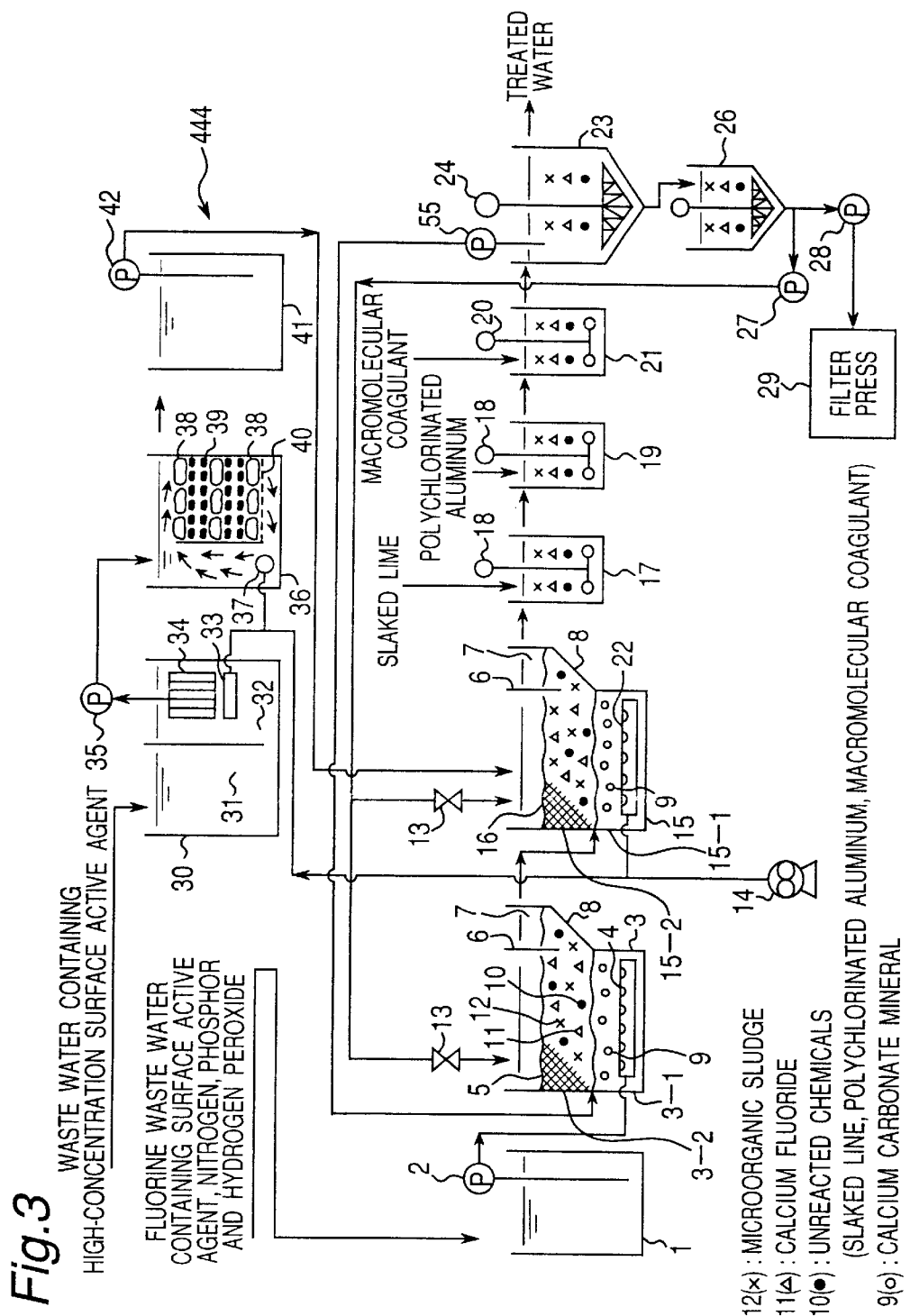

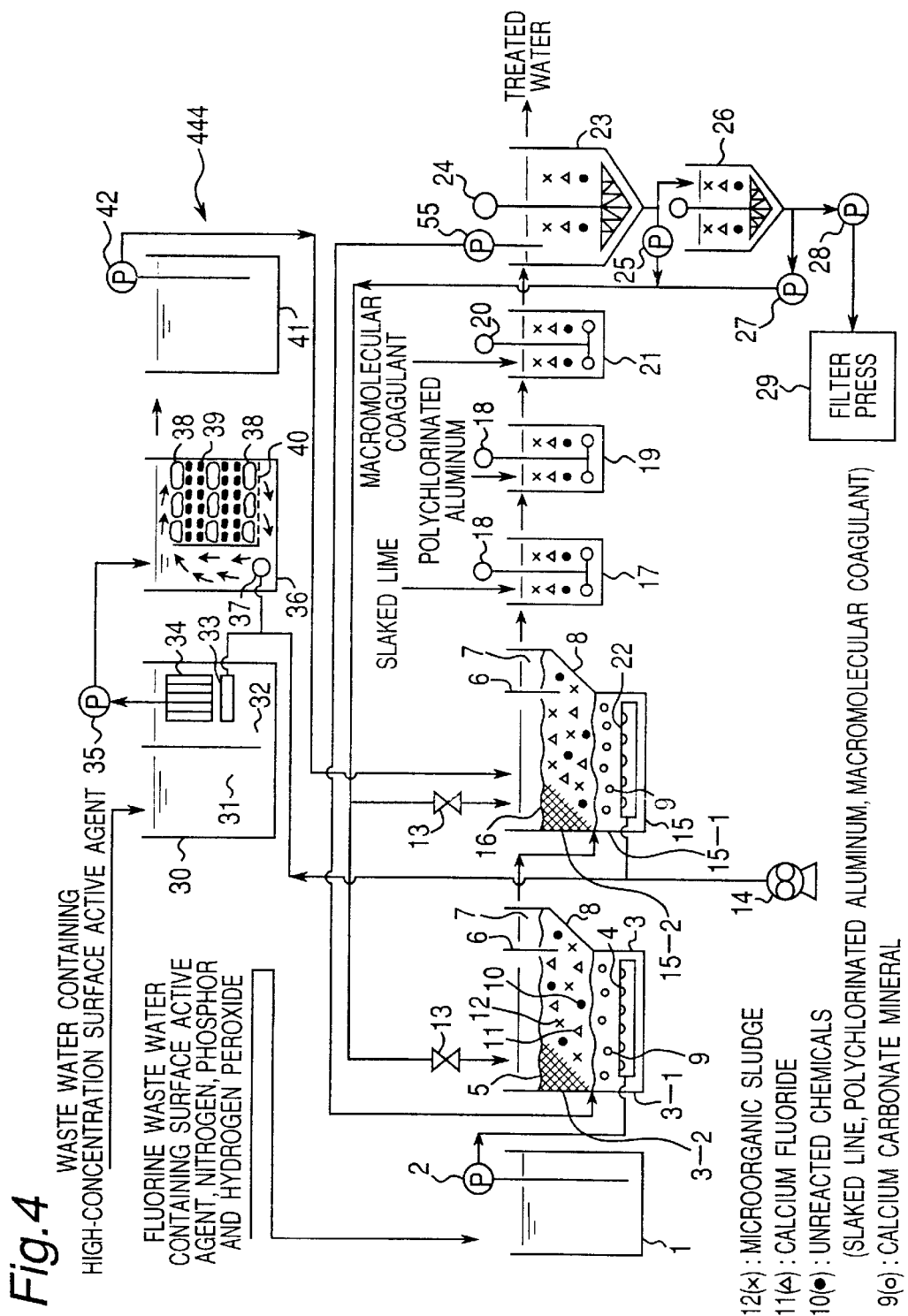

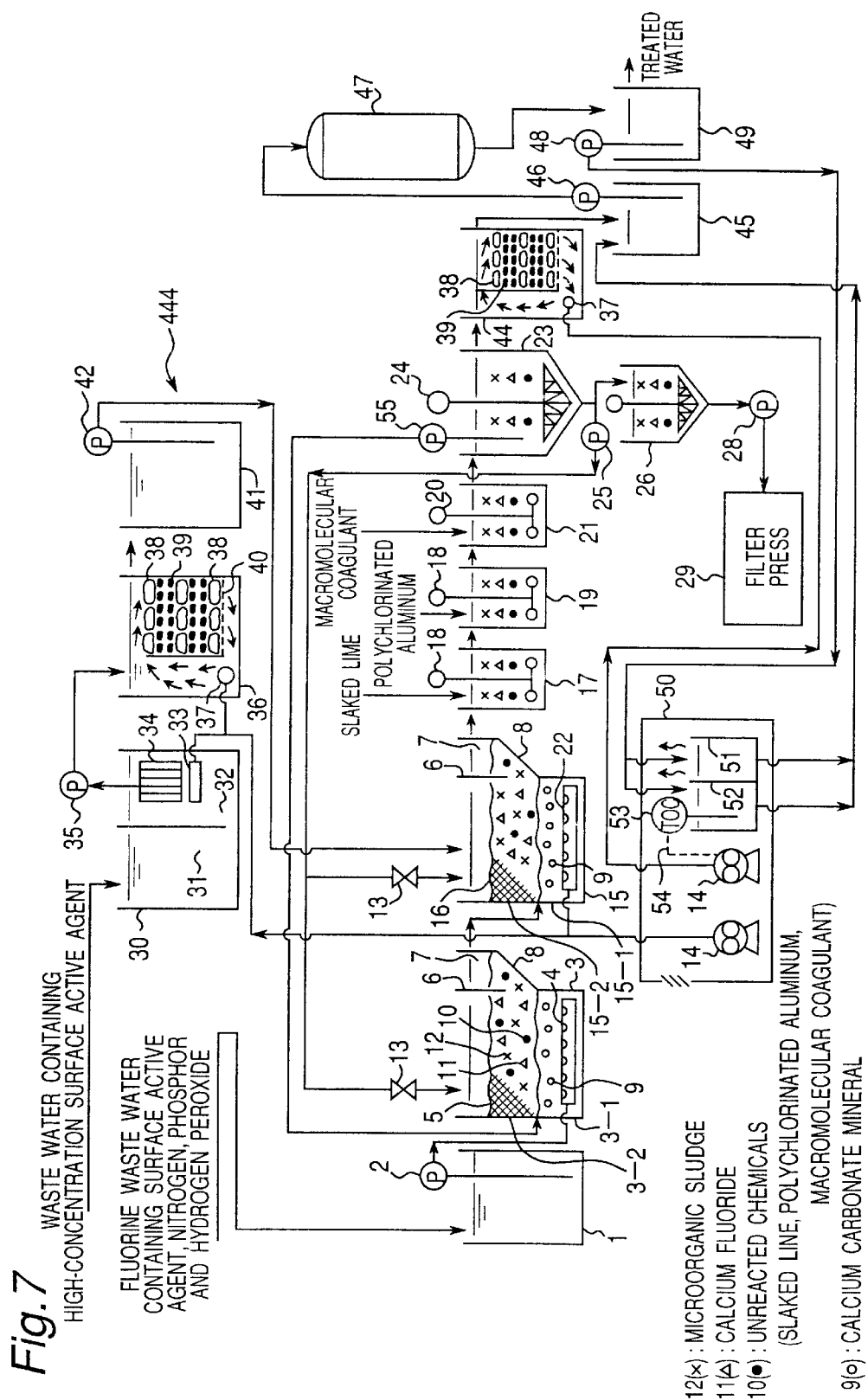

Fig.8A

WHEN FLUORINE WASTE WATER CONTAINING SURFACE ACTIVE AGENT, NITROGEN, PHOSPHOR AND HYDROGEN PEROXIDE HAS NORMAL CONCENTRATION

| TANK NAME | RETENTION TIME | TIMING (ELAPSED TIME) 1:00 2:00 3:00 4:00 5:00 6:00 7:00 8:00 9:00 10:00 11:00 12:00 13:00 14:00 15:00 |
|---|---|---|
| 1ST WATER TANK | 1HR. | |
| 2ND WATER TANK (ANAEROBIC TANK) | 2HR. | |
| 3RD WATER TANK (AEROBIC TANK) | 2HR. | |
| 4TH WATER TANK | 20MIN. | |
| 5TH WATER TANK | 20MIN. | |
| 6TH WATER TANK | 20MIN. | |
| 7TH WATER TANK (SEDIMENTATION TANK) | 3HR. | |
| 8TH WATER TANK (CONDENSATION TANK) | 5HR. | |
| 12TH WATER TANK | 3HR. | |
| PUMP PIT | 30MIN. | |
| BIOTIC ACTIVATED CARBON TOWER | 2HR. | |
| TREATMENT TANK | 30MIN. | |

Fig. 8B

WHEN FLUORINE WASTE WATER CONTAINING SURFACE ACTIVE AGENT, NITROGEN, PHOSPHOR AND HYDROGEN PEROXIDE HAS LOW CONCENTRATION

| TANK NAME | RETENTION TIME | TIMING (ELAPSED TIME) 1:00 2:00 3:00 4:00 5:00 6:00 7:00 8:00 9:00 10:00 11:00 12:00 13:00 14:00 15:00 |
|---|---|---|
| 1ST WATER TANK | 1HR. | |
| 2ND WATER TANK (ANAEROBIC TANK) | 1HR. | |
| 3RD WATER TANK (AEROBIC TANK) | 1HR. | |
| 4TH WATER TANK | 20MIN. | |
| 5TH WATER TANK | 20MIN. | |
| 6TH WATER TANK | 20MIN. | |
| 7TH WATER TANK (SEDIMENTATION TANK) | 3HR. | |
| 8TH WATER TANK (CONDENSATION TANK) | 5HR. | |
| 12TH WATER TANK | 3HR. | |
| PUMP PIT | 30MIN. | |
| BIOTIC ACTIVATED CARBON TOWER | 1HR. | |
| TREATMENT TANK | 30MIN. | |

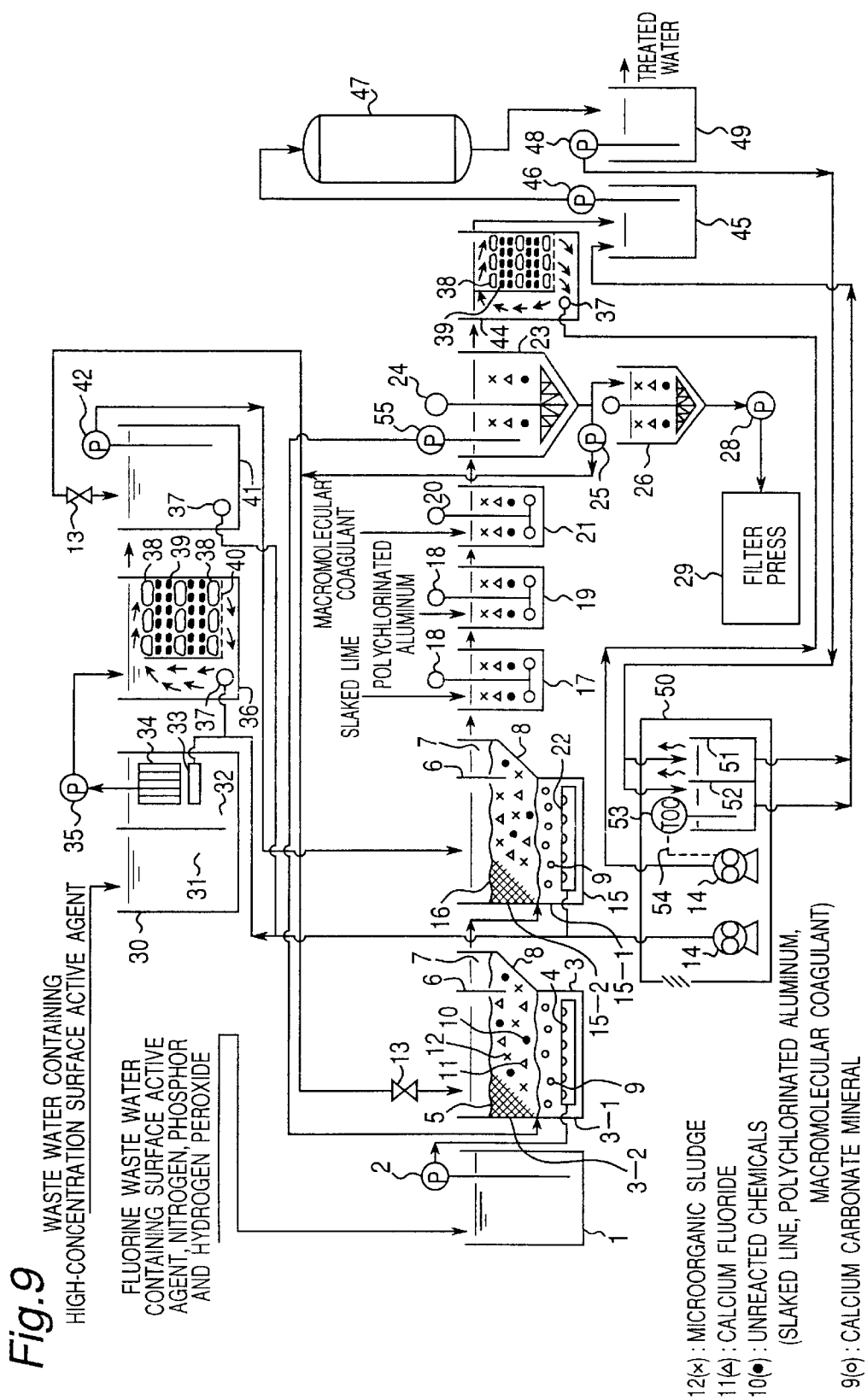

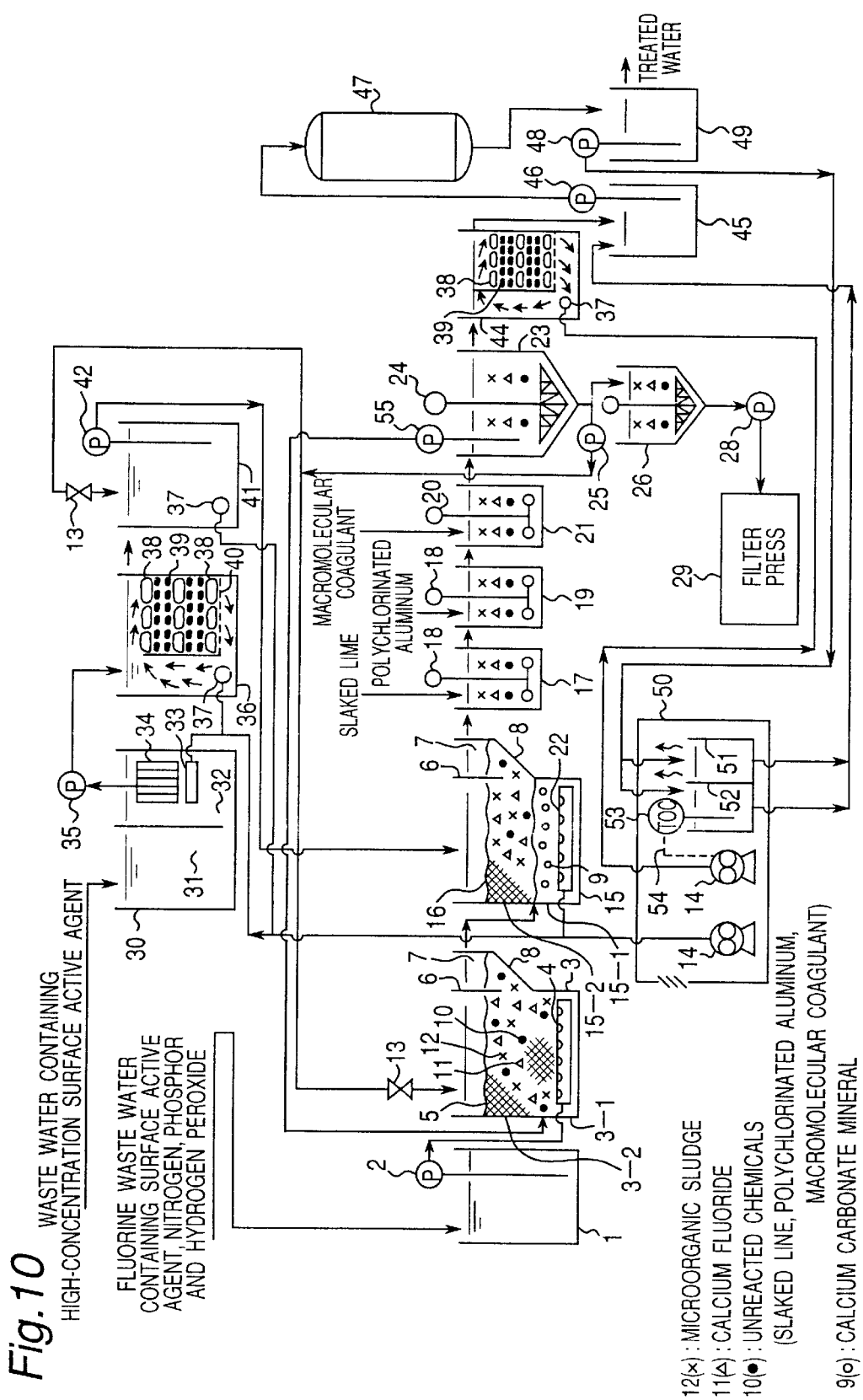

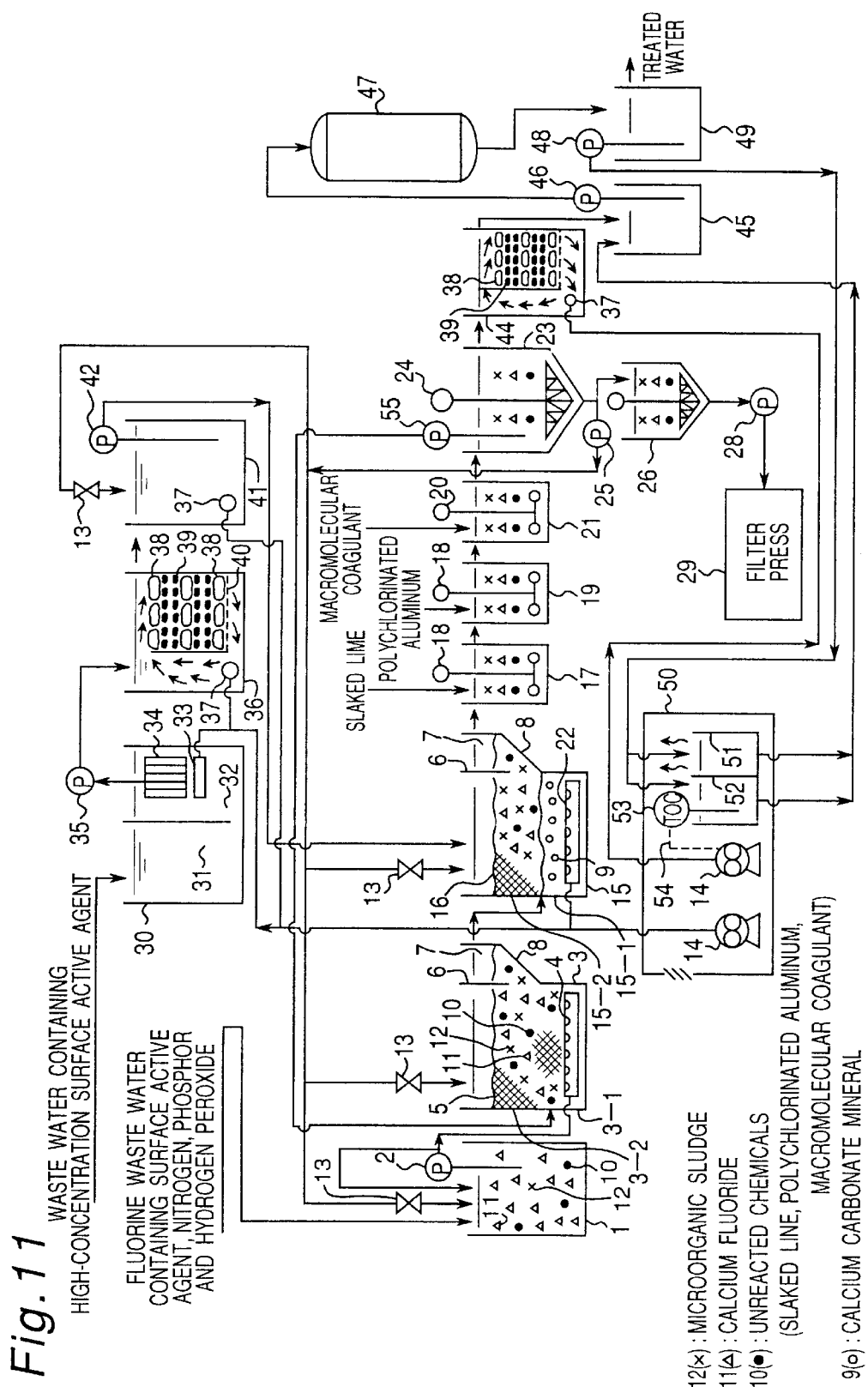

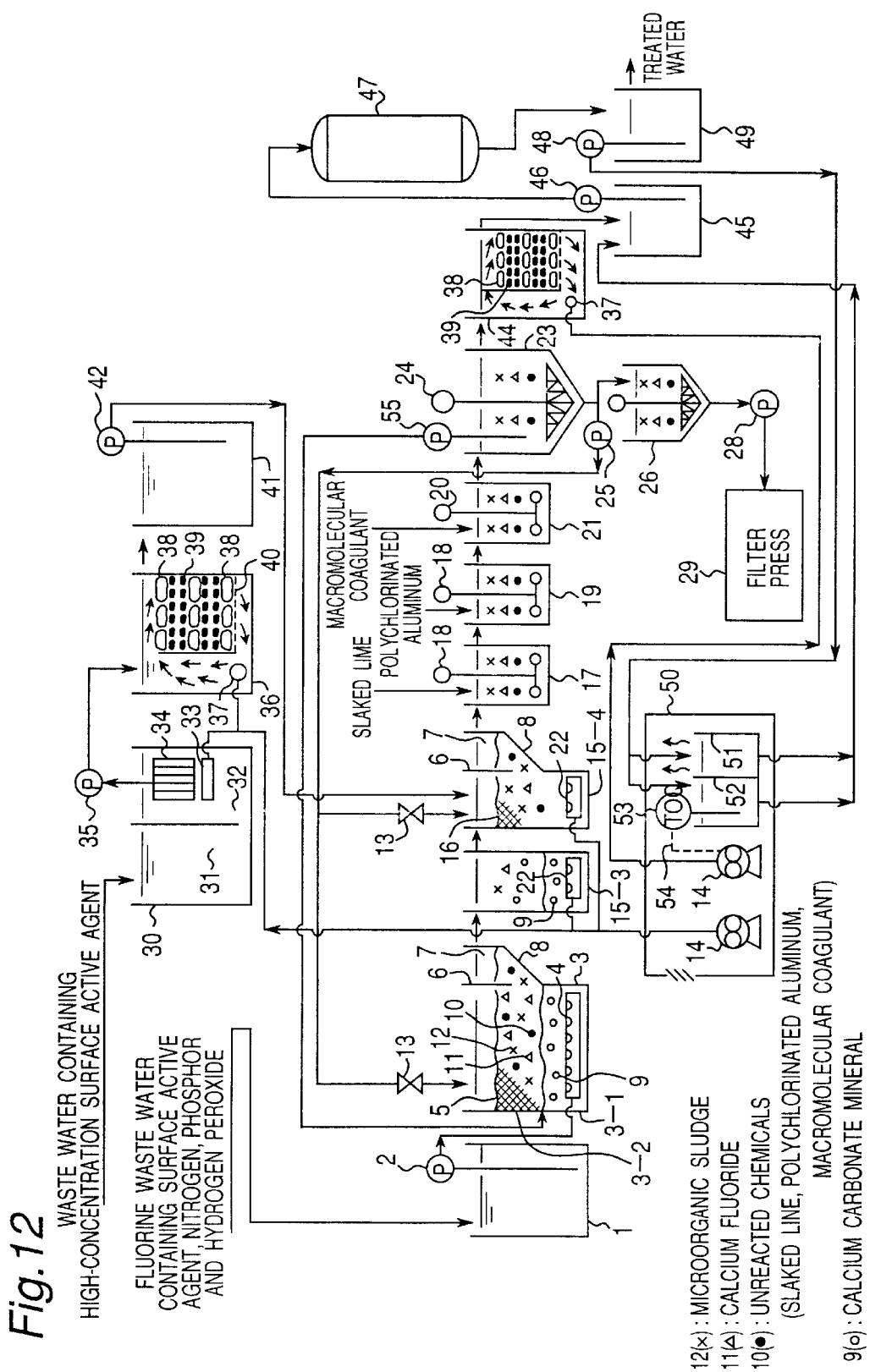

WASTE WATER TREATMENT METHOD BEING ABLE TO TREAT SURFACE ACTIVE AGENT, NITROGEN, HYDROGEN PEROXIDE AND PHOSPHOR WITH HIGH EFFICIENCY

This application is a division of application Ser. No. 09/432,599, filed Nov. 3, 1999, the entire content of which is hereby incorporated by reference in this application, now U.S. Pat. No. 6,375,837.

BACKGROUND OF THE INVENTION

The present invention relates to a waste water treatment method and waste water treatment equipment capable of treating the organic matter discharged from a semiconductor plant, a liquid crystal plant or the like, and in particular, fluorine waste water containing a surface active agent, nitrogen, phosphor and hydrogen peroxide of poor biodegradability. The present invention relates, in particular, to a waste water treatment method and waste water treatment equipment that generates little sludge (waste) and is able to treat the waste water by reusing chemicals.

In a semiconductor plant, liquid crystal plant or the like, surface active agents are mixed in various chemicals for use in the production apparatuses in line with the rapid progress in microstructure. It is general to use nitric acid, ammonia water, phosphoric acid, hydrogen peroxide and hydrofluoric acid in the manufacturing equipment of the semiconductor plant or the like. Among others, the amount of use of hydrofluoric acid tends to be generally great as compared with the other chemicals. For the above reasons, the fluorine waste water containing a surface active agent, nitrogen, phosphor, hydrogen peroxide and so on is discharged from the production rooms of the plant. It is to be noted that the fluorine waste water is an acid waste water that has fluorine as a main ingredient and contains a small amount of surface active agent, nitrogen, phosphor and hydrogen peroxide.

As described above, under the conditions of the rapid progress in microstructure of semiconductor devices, a surface active agent is used since aqueous cleaning by means of ultrapure water cannot sufficiently clean the minute portions due to the surface tension of water. For this reason, the surface active agent is mixed in the waste water.

As described above, in the semiconductor plant or the like, a method for cleaning the minute portions through the reduction of the surface tension by mixing a surface active agent into ultrapure water and a method for executing cleaning through the reduction of the surface tension by mixing a surface active agent into a variety of chemicals for cleaning use are gaining popularity. For example, a chemical such as buffered hydrofluoric acid containing a surface active agent is used. A variety of surface active agents to be mixed in the chemical are the important know-how of each chemical manufacturer, and newly-developed surface active agents are opportunely used. The newly-developed surface active agents include those of poor biodegradability in terms of the molecular formula, structural formula, effervescence, sterilizing performance and so on of the substance. Therefore, the conventional activated sludge method, catalytic oxidation method or the like as a representative of the biotic treatment become unable to cope with the decomposition treatment since the methods have a low microorganic concentration of about 2000 ppm to 5000 ppm.

Then, the latest report says that some surface active agents might become hormone disrupters, and prompt countermeasures are required.

The waste water also contains nitrogen and phosphor attributed to nitric acid, ammonia water and phosphoric acid, and it is required to treat the nitrogen and phosphor from the point of view of eutrophication and red tide. However, the general denitrification equipment and dephosphorization equipment disadvantageously require high initial cost and running cost.

The waste water also contains hydrogen peroxide, and in order to treat the hydrogen peroxide that serves as an oxidizing agent in the waste water, a treatment method using sodium bisulfite added as a reductant and a treatment method using activated carbon as a catalyst. However, those methods also require high initial cost and running cost.

In this age where environmental conservation is regarded as important, it is an important urgent problem that the enterprises should tackle to reuse the used chemicals and reduce waste generated from the plants for the achievement of cost reduction.

Conventionally, as a waste water treatment method for reusing the sludge including unreacted chemicals, there have been proposed the following methods (1), (2) and (3).

(1) First prior art: Japanese Patent Laid-Open Publication No. HEI 6-343974.

(2) Second prior art: Japanese Patent Laid-Open Publication No. HEI 8-197070.

(3) Third prior art: Japanese Patent Laid-Open Publication No. HEI 10-5769.

Each of the above three waste water treatment methods sends the sludge precipitated in the sedimentation tank back to the reaction tank or the coagulation tank, in which a stirrer is placed.

According to the first prior art, stirring is executed by stirring use air concurrently with stirring by the stirrer, however, the retention time is short. By comparing the stirring that continues for a short retention time (20 minutes, for example) by a stirrer to the stirring with a long reaction time (2 hours, for example) by air, it was discovered that the latter was more efficient in releasing calcium ions and aluminum ions from the hydroxide in the sludge particularly when utilizing again the sludge by sending back.

The fundament of the treatment of fluorine waste water is to form slightly-soluble calcium fluoride for the treatment. For the purpose of reducing the sludge that is the waste generated from the waste water treatment equipment, a method for using calcium carbonate mineral is adopted instead of the conventional slaked lime method for using slaked lime.

What is important in this case is that the fundament of the treatment of fluorine is to form slightly-soluble calcium fluoride and remove the same. If the slightly-soluble calcium fluoride is formed, then the calcium fluoride is not redissolved under either acid condition or alkali condition. That is, if the calcium fluoride that becomes the cores of flocs by reusing again and again the calcium agent (slaked lime or calcium carbonate mineral), then the waste generated from the waste water treatment equipment can be reduced. Furthermore, the chemicals can be reused to allow the waste water treatment to be efficiently achieved.

The sludge as the conventional waste also includes the aforementioned calcium fluoride, however, a large amount of unreacted slaked lime and unreacted coagulant has existed.

As a prior art that uses calcium carbonate, there is a fourth prior art reference (Japanese Patent Laid-Open Publication No. HEI 7-136667). According to this method, fluorine-containing water is made to serially flow through a plurality of towers filled with calcium carbonate, and after the outflow water of each tower filled with calcium carbonate is aerated, part of the water is made to flow again through the same tower filled with calcium carbonate. According to this fourth prior art example, by aerating the outflow water of each tower filled with calcium carbonate, $CO_2$ gas from $CaCO_3$ contained in this outflow water is discharged. By subsequently making the water flow again through the same tower filled with calcium carbonate, the amount of $CaCO_3$ that flows into the tower filled with calcium carbonate is reduced as far as possible. Through the above treatment, the amount of addition of the alkali agent of ammonia, ammonium fluoride or the like for the prevention of the collapse of the calcium carbonate filler material due to $CaCO_3$ can be reduced.

As a fifth prior art example, there is a "method for treating fluorine-containing organic waste water" disclosed in the prior art reference of Japanese Patent Laid-Open Publication No. HEI 5-4090. According to this treatment method, although the calcium carbonate mineral is not used, the water-soluble calcium compound of slaked lime, calcium chloride or the like is added to the fluorine-containing organic waste water so as to coagulate and precipitate the calcium fluoride. After adjusting pH of the supernatant liquid to 6.5 to 7.0, the water is brought in contact with fixed microorganic pellets to undergo an aeration treatment for the removal of BOD components. Subsequently, a coagulant is added to precipitate the microorganism leaked from the pellets together with the remaining fluorine compound. According to this fifth prior art example, the fluorine-containing organic waste water is subjected to a coagulo-sedimentation treatment, and thereafter the liquid pH is adjusted to 6.5 to 7.0 and then brought in contact with the fixed microorganic pellets. Therefore, the adhesion of calcium to the micropores of the fixed microorganic pellets is prevented, as a consequence of which a high rate of removal of fluorine and BOD can be achieved.

As a sixth prior art example, there is "waste water treatment equipment and waste water treatment method" disclosed in the prior art reference of Japanese Patent Laid-Open Publication No. HEI 9-174081. This sixth prior art example can treat fluorine waste water containing organic matter. As shown in FIG. 15, this waste water treatment equipment is provided with a first water tank 151 that has an upper portion 151A and a lower portion 151B. The first water tank upper portion 151A has an air diffusion pipe 152A and is filled with granular calcium carbonate mineral 157. The granular calcium carbonate mineral 157 of the first water tank upper portion 151A is made to strongly flow by aeration, by which the fluorine in the waste water chemically reacts with the calcium carbonate mineral 157 and becomes calcium fluoride, treating the fluorine in the waste water. On the other hand, a microorganism propagates on the surface of the granular calcium carbonate mineral 157 that has subsided from the first water tank upper portion 151A to the first water tank lower portion 151B, thereby biologically treating the organic matter in the waste water.

The granular calcium carbonate mineral 157 that has moved to the lowermost portion of the first water tank lower portion 151B moves toward the first water tank upper portion 151A while being mixed with the waste water by an air lift pump 155 placed in the lower portion 151B and chemically treats the fluorine in the waste water. A biotic sludge 156 and an inorganic sludge 200 comprised mainly of calcium fluoride, which are generated in the first water tank 151, are subjected to a coagulation treatment with polychlorinated aluminum added as an inorganic coagulant. Subsequently, each sludge moves to a sedimentation tank 163 so as to be subjected to solid-liquid separation into sludge as a precipitate and a treated water as a supernatant liquid.

As a seventh prior art example, there is "waste water treatment equipment and waste water treatment method" disclosed in the prior art reference of Japanese Patent Laid-Open Publication No. HEI 8-57498. This seventh prior art example can concurrently treat the waste water and exhaust gas, which contain fluorine and a surface active agent. According to this seventh prior art example shown in FIG. 16, a calcium carbonate mineral 146 is placed in a lower portion of a first reaction regulation tank 131, while the calcium carbonate mineral 146 and a plastic filler 148 are placed in an upper portion of the first reaction regulation tank 131. The calcium carbonate mineral 146 and charcoal 147 are placed in a lower portion of a second reaction regulation tank 132, while the charcoal 147 and a plastic filler 148 are placed in an upper portion of the second reaction regulation tank 132. A waste water containing fluorine and a surface active agent is firstly aerated and stirred in the lower portion of the first reaction regulation tank 131, then sprinkled in the upper portion of the first reaction regulation tank 131 and subsequently aerated and stirred in the lower portion of the second reaction regulation tank 132. The waste water is further sprinkled in the upper portion of the second reaction regulation tank 132, subsequently subjected to the coagulation treatment with added coagulant and then subjected to solid-liquid separation into a sludge as a precipitate and a supernatant liquid in a sedimentation tank 134. It is to be noted that the mixed sludge that includes inorganic sludge, organic sludge and biotic sludge as the sludges precipitated in the sedimentation tank 134 is sent back to the upper portion of the first reaction regulation tank 131 and sprinkled so as to be used for the treatment of the waste water and the exhaust gas.

As described above, the acid waste water discharged from the general semiconductor plant for fabricating integrated circuits includes fluorine as a main ingredient, organic matter such as a surface active agent as an ingredient having poor biodegradability, IPA (isopropyl alcohol), acetone, nitrogen attributed to nitric acid and ammonia water, phosphor attributed to phosphoric acid and hydrogen peroxide as an oxidizing agent.

Among others, with regard to, in particular, the surface active agent serving as the organic matter mixed in the chemicals, new products are opportunely developed with the progress in microstructure and mixed in the chemicals for use in a variety of production apparatuses. Accordingly, there are appearing products (i.e., surface active agents having poor biodegradability) that cannot easily be treated by microorganism at low microorganic concentration (2000 to 5000 ppm) by the conventional activated sludge method or the catalytic oxidation method.

In particular, according to the latest information, the aforementioned surface active agents, which might be a hormone disrupter, must be reliably decomposed by treatment.

Nitrogen and phosphor, which are the cause of eutrophication and red tide, are also required to be reliably treated.

The hydrogen peroxide in the waste water, which increases COD (Chemical Oxygen Demand) that is a discharge control item, must be controlled within a control value by treatment.

On the other hand, there is a tend toward substantially reducing the waste generated from each plant, and some plants have achieved the so-called zero emission for the total elimination of waste generated from the plants. Therefore, when treating the acid waste water in a semiconductor plant, there is needed a waste water treatment system for reducing the waste as far as possible.

A waste water treatment method for treating fluorine in the acid waste water has a first step for forming slightly-soluble calcium fluoride by adding the calcium agent of slaked lime, calcium carbonate mineral or the like, thereby treating the fluorine in the waste water to a concentration of about 20 to 40 ppm (this is the lower limit of treatment in the present circumstances). In a second step, the waste water obtained through the first step that can treat fluorine to a concentration of about 20 to 40 ppm at the utmost is thereafter treated down to the intended fluorine concentration (5 to 15 ppm) by adding an inorganic coagulant of polychlorinated aluminum or the like and subsequently adding a macromolecular coagulant.

However, in the second step, the fluorine concentration cannot be reduced to the intended concentration unless a large amount of inorganic coagulant such as polychlorinated aluminum or a large amount of macromolecular coagulant is added with respect to the amount of fluorine in the waste water (the achievement in the field of water treatment). Therefore, the unreacted polychlorinated aluminum, the macromolecular coagulant and so on precipitate together with the slightly-soluble calcium fluoride, and they become included in the sludge.

In view of the above, the unreacted polychlorinated aluminum and the unreacted macromolecular coagulant included in the sludge are sent back to the reaction tank or the coagulation tank so as to be reused. For example, the second prior art example (Japanese Patent Laid-Open Publication No. HEI 8-197070) sends the sludge back to the reaction tank.

However, those tanks, where stirring is executed by the stirrer, have small effect for loosening the sludge and have a short retention time. Therefore, the unreacted chemicals from the sludge cannot completely be regenerated as calcium ions and aluminum ions, and this has led to poor regeneration efficiency.

The third prior art example (Japanese Patent Laid-Open Publication No. HEI 10-5769) sends the sludge back to the coagulation tank that has a short retention time similarly to the reaction tank, instead of the reaction tank. This method has the problem that the sludge does not easily loosen, resulting in poor regeneration efficiency.

In view of the above, as an eighth prior art example, there is the one shown in FIG. 18. This eighth prior art example is a prior art method for treating a fluorine waste water containing a surface active agent, phosphor and hydrogen peroxide using general calcium carbonate mineral. The surface active agent serving as the organic matter in the waste water is somewhat decomposed by the aerobic microorganism in a second water tank 193. However, for the reason that the microorganic concentration is low and the biodegradability of the surface active agent is poor in the second water tank 193, it has been impossible to secure a sufficient ratio of decomposition and removal of the surface active agent. Specifically, the removal ratio of the surface active agent in the second water tank 193 is intended to be 50% or higher, whereas the waste water treatment equipment shown in FIG. 18 has not been able to secure a surface active agent removal ratio of 50%.

The hydrogen peroxide in the waste water is more or less decomposed by the anaerobic microorganism propagating in the third water tank 195 through the sixth water tank 198, whereas the removal ratio regarding the decomposition of hydrogen peroxide has practically been not greater than 50%.

Although an removal ratio of not lower than 90% of phosphor in the waste water has been able to be achieved since slaked lime is added to the third water tank 195. However, in order to secure the removal ratio, there has been the problem that the slaked lime is required to be excessively added in terms of concentration more than is needed for phosphor in the waste water. That is, the slaked lime added to the third water tank 195 tends to easily flow without sinking, and the unreacted slaked lime flows out of the third water tank 195 toward the fourth water tank 196 since the reaction time has a duration of not longer than one hour instead of a duration of not shorter than several hours.

The same thing can be said for not only the slaked lime but also the polychlorinated aluminum added to the fourth water tank 196 and the macromolecular coagulant added to the fifth water tank 197. As a result, the unreacted coagulant sludge (i.e., hydroxide sludge of calcium hydroxide, aluminum hydroxide and so on) attributed to the slaked lime, polychlorinated aluminum and macromolecular coagulant exists in the sludge precipitated in the sixth water tank 198, causing an increase in the amount of generated sludge.

As described above, according to the waste water treatment method of the eighth prior art example, the amount of generated sludge is reduced as compared with the waste water treatment method for executing treatment with the slaked lime and the coagulant without using the calcium carbonate mineral 191. However, the unreacted slaked lime and the unreacted coagulant are still contained in the sludge. Therefore, this waste water treatment method is not the most appropriate waste water treatment method in the current age of waste reduction, and the reuse of the unreacted slaked lime and the unreacted coagulant has been a big problem.

SUMMARY OF THE INVENTION

Accordingly, the present invention has the following objects (1) through (5).

(1) An object is to highly efficiently treat the surface active agent in the waste water.

(2) An object is to efficiently treat the nitrogen in the waste water.

(3) An object is to reuse the unreacted polychlorinated aluminum and macromolecular coagulant.

(4) An object is to efficiently treat the hydrogen peroxide and phosphor in the waste water.

(5) An object is to reduce the waste generated from the waste water treatment equipment.

In order to achieve the aforementioned object, there is provided a waste water treatment method for treating a fluorine waste water containing organic matter, nitrogen, phosphor and hydrogen peroxide by introducing the waste water into an anaerobic tank and an aerobic tank, comprising: a calcium carbonate mineral placed in the anaerobic tank; a biologically treated water of another system introduced into the aerobic tank; and a calcium carbonate mineral placed in the aerobic tank.

According to this constitution of the present invention, the organic matter can be treated in the anaerobic tank. If nitrate nitrogen exists, then the denitrification can be achieved by using the organic matter as a hydrogen donor. The organic matter in the waste water can be treated in the aerobic tank, and if ammoniacal nitrogen and nitrite nitrogen exist in the waste water, then the nitric substances can be aerobically oxidized to the nitrate nitrogen. By the microorganism included in the biologically treated water of another system introduced into the aerobic tank, the organic matter can be efficiently biologically treated.

In an embodiment of the present invention, the, organic matter is a surface active agent having poor biodegradability.

According to this embodiment, the biologically treated water introduced into the aerobic tank includes a microorganism. Therefore, the surface active agent having poor biodegradability can be more easily decomposed than in the case where the surface active agent is treated by only the microorganism that is naturally generated and propagated.

In an embodiment of the present invention, the biologically treated water is a treated water obtained by biologically treating a waste water containing a high-concentration surface active agent.

According to this embodiment, the biologically treated water of another system is the treated water obtained by biologically treating the waste water containing a high-concentration surface active agent. Therefore, the microorganism included in the biologically treated water is the microorganism more appropriate for the treatment of the surface active agent. The microorganism is plentifully contained in the biologically treated water, and therefore, the surface active agent in the waste water can be efficiently treated.

In an embodiment of the present invention, the biologically treated water is a treated water obtained by biologically treating a waste water containing a developing solution.

According to this embodiment, the biologically treated water is the treated water obtained by biologically treating the waste water containing a developing solution. This waste water containing a developing solution generally includes a high-concentration surface active agent, and the surface active agent in the waste water can be efficiently treated. The waste water containing a developing solution exists in almost all the IC plants, and the waste water can be treated by effectively utilizing the biologically treated water from the biological treatment equipment of another system for biologically treating the waste water containing a developing solution.

Also, there is provided waste water treatment equipment wherein a fluorine waste water containing organic matter, nitrogen, phosphor and hydrogen peroxide is chemically and biologically treated and thereafter treated by being introduced into a biotic activated carbon tank and a biotic activated carbon tower having a biotic activated charcoal and a biotic activated carbon.

According to this constitution of the present invention, the waste water is chemically and biologically treated and thereafter further biologically and physically treated by the biotic activated carbon tank and the biotic activated carbon tower having a biotic activated carbon and a biotic activated charcoal. Therefore, in particular, the organic matter can be highly and reliably treated.

The biotic activated carbon tank means a treatment tank in which both the Bincho charcoal that serves as a charcoal and the activated carbon are placed and the microorganisms are propagated on the surfaces of these fillers, providing the practical effect of regenerating the organic matter component absorbed by the Bincho charcoal and the activated carbon. The biotic activated carbon tower means an activated carbon tower in which the microorganism is propagated on the activated carbon and the organic matter adsorbed by the activated carbon is treated by the propagated microorganism, providing the practical effect of automatically regenerating the activated carbon. Therefore, the biotic activated carbon tank and the biotic activated carbon tower are not required to be regenerated even after a lapse of a specified period. In contrast to this, in the activated carbon tower of the general waste water treatment equipment, the activated carbon is taken out with the frequency of once three to six months and regenerated in the other place.

In an embodiment of the present invention, the anaerobic tank has an upper portion constructed of an anaerobic sludge zone and a lower portion constructed of a calcium carbonate mineral zone, and the aerobic tank has an upper portion constructed of an aerobic sludge zone and a lower portion constructed of a calcium carbonate mineral zone.

According to this embodiment, the nitrate nitrogen can be denitrified in the anaerobic sludge zone in the upper portion of the anaerobic tank, and the organic matter and the hydrogen peroxide can be further treated. The fluorine can be treated in the calcium carbonate mineral zone in the lower portion of the anaerobic tank. The organic matter can be treated in the aerobic sludge zone in the upper portion of the aerobic tank, and the fluorine can be treated in the calcium carbonate mineral zone in the lower portion of the aerobic tank.

In an embodiment of the present invention, the anaerobic sludge zone in the upper portion of the anaerobic tank has a sludge that includes an unreacted slaked lime, an unreacted polychlorinated aluminum, an unreacted macromolecular coagulant, a generated calcium fluoride and a microorganism, and the aerobic sludge zone in the upper portion of the aerobic tank has a sludge that includes an unreacted slaked lime, an unreacted polychlorinated aluminum, an unreacted macromolecular coagulant, a generated calcium fluoride and a microorganism.

According to this embodiment, the sludge in the anaerobic sludge zone in the upper portion of the anaerobic tank includes the unreacted slaked lime, unreacted polychlorinated aluminum, unreacted macromolecular coagulant, generated calcium fluoride and microorganism. Therefore, phosphor can be treated as calcium phosphate by the unreacted slaked lime. The calcium fluoride formed through the reaction of fluorine with the calcium carbonate mineral in the lower portion of the anaerobic tank can be formed into larger and more stable flocs by the unreacted polychlorinated aluminum and the unreacted macromolecular coagulant.

The sludge in the aerobic sludge zone in the upper portion of the aerobic tank is a sludge that includes the generated calcium fluoride and the microorganism. Therefore, the organic matter can be aerobically treated.

The sludge in the aerobic sludge zone in the upper portion of the aerobic tank includes the unreacted slaked lime, unreacted polychlorinated aluminum, unreacted macromolecular coagulant, generated calcium fluoride and microorganism. Therefore, phosphor can be treated as calcium phosphate by the unreacted slaked lime similarly to the anaerobic tank. The calcium fluoride formed through the reaction of fluorine with the calcium carbonate mineral in the lower portion of the aerobic tank can be formed into larger and more stable flocs by the unreacted polychlorinated aluminum and the unreacted macromolecular coagulant. The sludge in the aerobic sludge zone in the upper portion of the aerobic tank is a sludge that includes the generated calcium fluoride and the microorganism. Therefore, the organic matter can be aerobically treated.

As described above, according to this embodiment, the waste water can be treated without using any new chemical in both the anaerobic tank and the aerobic tank.

In an embodiment of the present invention, the sludge is a return sludge from a sedimentation tank of waste water treatment equipment.

According to this embodiment, the sludge is the return sludge from the sedimentation tank of the waste water treatment equipment. Therefore, the sludge including the unreacted slaked lime, unreacted polychlorinated aluminum, unreacted macromolecular coagulant, generated calcium fluoride and microorganism can be easily secured as the return sludge from the waste water treatment equipment through no special process and utilized for waste water treatment.

The return sludge has an increased sludge concentration through the sedimentation process in the sedimentation tank, and in addition, the sedimentation tank has no aeration process. Therefore, the microorganisms mainly comprised of the anaerobic microorganism are propagating in this return sludge. Therefore, if the sludge is sent back to the anaerobic tank (second water tank), then the waste water can be efficiently treated by this return sludge having a high sludge concentration.

Since there is existing no aeration process in the anaerobic tank (second water tank), the degree of anaerobic property is increased further than in the sedimentation tank. Consequently, the anaerobic microorganism propagates and increases to allow the waste water to be anaerobically treated. The return sludge from the sedimentation tank is also sent back and introduced into the aerobic tank (third water tank). Since the aeration process is existing in this aerobic tank, the aerobic microorganism gradually propagates and increases to allow the waste water to be aerobically treated.

In an embodiment of the present invention, the microorganism in the anaerobic sludge zone of the anaerobic tank is an anaerobic microorganism, and the microorganism in the aerobic sludge zone of the aerobic tank is an aerobic microorganism.

According to this embodiment, the microorganism existing in the anaerobic sludge zone of the anaerobic tank is the anaerobic microorganism. Therefore, the nitrate nitrogen can be denitrified using the organic matter in the waste water as a hydrogen donor, and the surface active agent serving as the organic matter can also be concurrently treated. Furthermore, the hydrogen peroxide can be treated by the reducibility owned by the anaerobic microorganism. The microorganism existing in the aerobic sludge zone of the aerobic tank is the aerobic microorganism. Therefore, the ammoniacal nitrogen and the nitrite nitrogen in the waste water can be oxidized to the nitrate nitrogen, and the surface active agent serving as the organic matter can also be concurrently treated by the aerobic microorganism.

Also, there is provided waste water treatment equipment comprising: a first water tank into which the fluorine waste water containing organic matter, nitrogen, phosphor and hydrogen peroxide is firstly introduced; a second water tank in which a calcium carbonate mineral is placed and into which the return sludge is introduced; a third water tank which has a stirring means and a calcium carbonate mineral placed therein and into which the return sludge and the biologically treated water are introduced and mixed; a fourth water tank to which slaked lime is added; a fifth water tank to which polychlorinated aluminum is added; a sixth water tank to which a macromolecular coagulant is added; a seventh water tank that serves as a sedimentation tank; and an eighth water tank that serves as a condensation tank, the waste water to be treated being sequentially introduced into the first, second, third, fourth, fifth, sixth, seventh and eighth water tanks.

According to this constitution, the fluorine in the waste water can be treated as calcium fluoride by the calcium carbonate mineral placed in the second water tank, and the waste water can also be treated by the components in the return sludge.

The fluorine in the waste water can be efficiently treated as calcium fluoride by the calcium carbonate mineral placed in the third water tank by stirring the waste water by the stirring means. Furthermore, the waste water that is being stirred can be efficiently treated by the components in the return sludge to the third water tank. Furthermore, the biologically treated water is Introduced and mixed in the third water tank, and therefore, the microorganism in the biologically treated water facilitates the treatment of, in particular, the organic matter.

In the fourth water tank to which slaked lime is added, the phosphor in the waste water can be treated into calcium phosphate.

In the fifth water tank to which polychlorinated aluminum is added, the formed minute calcium fluoride and the calcium phosphate come to have a floc form.

In the sixth water tank to which a macromolecular coagulant is added, the flocs formed in the fifth water tank can be formed into larger stable flocs.

In the seventh water tank (sedimentation tank), a treated water can be obtained as a supernatant liquid by precipitating the sludge that serves as a solid matter in the waste water.

In the eighth water tank (condensation tank), the sludge that serves as the solid matter precipitated in the seventh water tank (sedimentation tank) can be further condensed to allow the sludge concentration to be increased. In addition, the sedimentation tank and the condensation tank are supplied with no oxygen, and therefore, the anaerobic microorganism can be cultured and propagated in the sludge.

Also, there is provided waste water treatment equipment comprising: a first water tank into which the fluorine waste water containing organic matter, nitrogen, phosphor and hydrogen peroxide is firstly introduced; a second water tank in which a calcium carbonate mineral is placed and into which the return sludge is introduced; a third water tank which has a stirring means and a calcium carbonate mineral placed therein and into which the return sludge and the biologically treated water are introduced and mixed; a fourth water tank to which slaked lime is added; a fifth water tank to which polychlorinated aluminum is added; a sixth water tank to which macromolecular coagulant is added; a seventh water tank that serves as a sedimentation tank; an eighth water tank that serves as a condensation tank; a twelfth water tank which has a stirring means and charcoal and activated carbon placed therein and into which a supernatant water from the seventh water tank is introduced; and a biotic activated carbon tower.

According to this constitution, the first through eighth water tanks have quite the same operations and effects as those of the last constitution.

This constituion differs from the last one in the following points (1) and (2). (1) The stirring means is provided, and the supernatant liquid from the seventh water tank (sedimentation tank) is introduced into the twelfth water tank filled with the charcoal and the activated carbon, the charcoal and the activated carbon adsorbing the organic matter such as the surface active agent in the waste water that can be hardly biologically decomposed. (2) After the adsorption by the charcoal and the activated carbon, the surface active agent can be biologically decomposed by the microorganism propagating on the surfaces of the charcoal and the activated carbon. The twelfth water tank filled with the charcoal and the activated carbon is arranged before the biotic activated carbon tower. Therefore, the twelfth water tank serves as the pretreatment tank to allow the function of the biotic activated carbon tower to be consistently maintained. This reliably obviates the need for the activated carbon regenerating work in the biotic activated carbon tower.

In an embodiment of the present invention, the waste water treatment equipment further comprises a sludge returning means for sending the sludge precipitated in the seventh water tank or the sludge condensed in the eighth water tank or both kinds of sludge back to an upper portion of the second water tank.

According to this embodiment, the sludge precipitated in the seventh water tank or the sludge condensed in the eighth water tank or both of them are sent back to the upper portion of the second water tank. Therefore, the microorganic concentration in the upper portion of the second water tank can be increased. In addition, this microorganism has passed through the seventh water tank (sedimentation tank) and the eighth water tank (condensation tank). Therefore, the anaerobic microorganism becomes dominant to allow the anaerobic sludge zone to be constructed in the upper portion of the second water tank. If the anaerobic sludge zone is constructed, then the nitrate nitrogen ($NO_3$—N) in the waste water can be denitrified into $N_2$ gas.

In an embodiment of the present invention, the waste water treatment equipment further comprises a first biological treatment means for biologically treating the waste water containing a high-concentration surface active agent by means of a high-concentration microorganism with a separation membrane; and a second biological treatment means for biologically treating the treated water from the first biological treatment means by means of a charcoal and activated carbon water tank filled with charcoal and activated carbon, the treated water treated by the first and second biological treatment means serving as a biologically treated water to be introduced into the third water tank.

According to this embodiment, the waste water containing a high-concentration surface active agent is biologically treated by the high-concentration microorganism with the separation membrane. Therefore, the surface active agent that can be easily biologically treated is removed, and the waste water including the surface active agent that can hardly be biologically treated passes through the separation membrane. Then, the filtered waste water flows into the charcoal and activated carbon water tank filled with the charcoal and the activated carbon. In this charcoal and activated carbon water tank, the microorganism for decomposing the surface active agent that can hardly be biologically treated is propagating using the charcoal and the activated carbon as a carrier for fixation. That is, the microorganism for decomposing the surface active agent that can hardly be biologically treated is propagated and cultured in the water tank filled with the charcoal and the activated carbon, allowing the biologically treated water capable of more efficiently treating the surface active agent in the waste water to be introduced into the third water tank(aerobic tank)

That is, the microorganism that has been accustomed to the surface active agent that is hardly biologically decomposed has a capability for decomposing every sort of surface active agent. By mixing the biologically treated water that includes the microorganism having an excellent degradability to the surface active agent into the third water tank (aerobic tank), the surface active agent in the waste water can be easily efficiently treated.

In an embodiment of the present invention, the waste water treatment equipment further comprises an eleventh water tank for mixing at least one of the sludge precipitated in the seventh water tank and the sludge condensed in the eighth water tank with the biologically treated water from the first and second biological treatment means and thereafter introducing the resulting mixture into the third water tank.

According to this embodiment, the biologically treated water and at least one of the sludge precipitated in the seventh water tank and the sludge condensed in the eighth water tank are mixed with each other in the eleventh water tank and thereafter introduced into the third water tank. Therefore, the microorganism is fixed in the sludge, and the surface active agent in the waste water can be treated by the microorganism adapted to the decomposition treatment. Therefore, the surface active agent can be efficiently treated. That is, the microorganism having an excellent degradability of the surface active agent is fixed in the sludge in the eleventh water tank of another system and then cultured and propagated. Thereafter, the sludge is introduced into the third water tank so as to more efficiently treat every surface active agent in the waste water.

In an embodiment of the present invention, the eleventh water tank mixes at least one of the sludge precipitated in the seventh water tank and the sludge condensed in the eighth water tank with the biologically treated water from the first and second biological treatment means under aerobic conditions and thereafter introduces the resulting mixture into the third water tank.

According to this embodiment, the biologically treated water and at least one of the sludge precipitated in the seventh water tank and the sludge condensed in the eighth water tank are mixed with each other in the eleventh water tank and thereafter introduced into the third water tank. Therefore, the aerobic microorganism is fixed in the sludge, and the surface active agent in the waste water can be treated by the aerobic microorganism adapted to the decomposition treatment, allowing the surface active agent to be efficiently treated. That is, the aerobic microorganism having an excellent degradability of the surface active agent is preparatorily fixed in the sludge in the eleventh water tank of another system and then cultured and propagated. Thereafter, the sludge is introduced into the third water tank so as to more efficiently treat every surface active agent in the waste water.

According to this embodiment, the aerobic microorganism that has preparatorily been accustomed to the decomposition of the surface active agent is fixed in the sludge. Therefore, if the microorganism is introduced into the third water tank (aerobic tank), then every sort of surface active agent can be treated more efficiently.

In an embodiment of the present invention, the eleventh water tank mixes at least one of the sludge precipitated in the seventh water tank and the sludge condensed in the eighth water tank with the biologically treated water from the first and second biological treatment means under anaerobic conditions and thereafter introduces the resulting mixture into the second water tank.

According to this embodiment, the biologically treated water and at least one of the sludge precipitated in the seventh water tank and the sludge condensed in the eighth water tank are mixed with each other under anaerobic conditions in the eleventh water tank and thereafter introduced into the second water tank. Therefore, the anaerobic microorganism is fixed in the sludge in the eleventh water tank. Subsequently, this sludge is introduced into the third water tank. Therefore, the treatment can be activated by the anaerobic microorganism adapted to the decomposition treatment of the surface active agent in the waste water, allowing the surface active agent to be efficiently treated.

Since the sludge zone is formed in the second water tank, the concentration of the anaerobic microorganism that has been accustomed to the decomposition of the surface active agent can be kept high. Consequently, not only the surface active agent in the waste water but also the nitrate nitrogen and hydrogen peroxide can be more efficiently treated.

That is, according to this embodiment, the anaerobic microorganism having an excellent degradability of the surface active agent is preparatorily fixed under anaerobic conditions in the sludge in the eleventh water tank of another system and cultured and propagated. Thereafter, the anaerobic sludge is introduced into the second water tank. With this arrangement, every surface active agent in the waste water, including the nitrate nitrogen and hydrogen peroxide that can be treated by the high-concentration anaerobic microorganism, can be more efficiently treated.

In an embodiment of the present inventioin, the treated water from the biotic activated carbon tower is introduced into a biotic monitoring water tank provided with a TOC (Total Organic Carbon) meter, and the stirring means of the twelfth water tank is controlled by the TOC concentration of the biotic monitoring water tank.

According to this embodiment, the surface active agent concentration can be easily controlled by replacing the surface active agent concentration that requires much time for the measurement with the TOC concentration that can be automatically measured in a short time. That is, by measuring the TOC concentration that can be consistently automatically measured on line to the ppb order instead of the surface active agent concentration that requires much time for the measurement, more accurate waste water treatment water quality control can be achieved.

If the TOC concentration is too high to achieve a specified treatment condition in the biotic monitoring water tank, i.e., if the water quality is bad, then the stirring means of the twelfth water tank is controlled to allow the treatment performance to be improved.

The surface active agents include an anionic surface active agent, a cationic surface active agent and a nonionic surface active agent. An high-grade measuring device is necessary for measuring the concentration in the waste water, but currently no practical automatic measurement of such high-grade has been established. That is, two to three days are necessary at the earliest after sampling the waste water. The on-line automatic measurement is to sample the waste water by a pump, introduce the waste water into an automatic measurement device through piping and measure the specified component in the waste water. It is to be noted that the items that can be currently automatically measured on line include COD, a fluorine concentration and so on besides TOC.

In an embodiment of the present invention, the biotic monitoring water tank is provided in a blower chamber and an aquatic living thing is bred in the biotic monitoring water tank.

According to this embodiment, the biotic monitoring water tank is provided for the blower chamber. Therefore, the waste water can be stably evaporated and condensed by the heat generated from the blower itself stably throughout the year without providing any new evaporation and condition equipment. Then, the waste water is introduced into the biotic monitoring water tank and condensed there. Therefore, even if the water quality of the treated water at the exit of the biotic activated carbon tower has low values with regard to all the items that may influence the living thing, the influence on the living thing can be swiftly confirmed by increasing the concentration of harmful substances by condensation.

Furthermore, the aquatic living thing is bred in the biotic monitoring water tank. Therefore, if an aquatic living thing that is influenced by the surface active agent even in low concentration and an aquatic living thing sensitive to the environment are selected, then the influence of the treated water including the chemical substances such as the surface active agent on the living things can be comprehensively confirmed.

In an embodiment of the present invention, the stirring means is a pneumatic stirring means for executing stirring by air.

According to this embodiment, the stirring means of the twelfth water tank is the pneumatic stirring means. Therefore, the inside of the tank can be stirred by the upward flow of the aeration by air, and the organic matter such as the surface active agent in the waste water can be biologically treated by the aerobic microorganism that is propagating on the surfaces of the charcoal and the activated carbon. By virtue of the aerobic microorganism propagating on the surface of the activated carbon in the biotic activated carbon tower in the next process, the dissolved oxygen concentration in the waste water in the twelfth water tank can be increased. As a result, the waste water having a high dissolved oxygen concentration can be introduced into the biotic activated carbon tower.

Therefore, since the stirring means is provided by the pneumatic stirring, the organic matter adsorbed by the activated carbon can be treated by the aerobic microorganism propagating on the surface of the activated carbon without taking out nor regenerating the activated carbon in the biotic activated carbon tower, and the state in which the activated carbon can always be regenerated can be practically maintained. It is to be noted that the biotic activated carbon means the activated carbon in a state in which the organic matter adsorbed by the activated carbon is treated by the microorganism propagating on the surface of the activated carbon as if the activated carbon is regenerated.

In an embodiment of the present invention, any one of a group consisting of: a snail such as a marsh snail; a guppy; and Oryzias latipes is selected as the aquatic living thing.

According to this embodiment, any of the snail such as a marsh snail, guppy and Oryzias latipes is selected as the aquatic living thing. Therefore, only if the water temperature and water quality of the waste water are controlled, the eggs of the aquatic living thing can be hatched within a short period of one to three months, and the influence of the chemical substances of the surface active agent and the like on the alternation of generations of the aquatic living thing can be confirmed.

That is, according to these embodiments, the optimum water for breeding the aquatic living thing is made by maintaining the water temperature of the biotic monitoring water tank utilizing the heat generated from the blower and treating the waste water by the twelfth water tank (biotic activated carbon tank) and the biotic activated carbon tower.

Therefore, even if no decision is made as to whether or not a chemical substance in the waste water might be a hormone disrupter, then it can be easily confirmed whether or not the chemical substance such as the surface active agent in the waste water might be a hormone disrupter since the aquatic living thing exhibits alternation of generations several times within a short period in the environment where the eggs hatch most easily. It has already been discovered through experiments that the aquatic living things can be easily bred in the treated water treated by the aforementioned biotic activated carbon tank and the biotic activated carbon tower. The aquatic living thing means all sorts of living things such as fishes and snails living in the waste water.

In an embodiment of the present invention, the return sludge is introduced into the first water tank.

According to this embodiment, the return sludge is introduced into the first water tank. With this arrangement, the waste water can be pretreated by the unreacted slaked lime and the unreacted coagulant even if the water quality of the waste water abruptly changes to the higher concentration side. Therefore, the posttreatment after the pretreatment can be stabilized. The return sludge is in a muddy state. However, the unreacted slaked lime and the unreacted coagulant sludge can be dissolved in the acid waste water so as to be brought into a solution state, or a state in which they can easily react. According to this embodiment, the return sludge is introduced into all of the first, second and third water tanks. Therefore, the unreacted slaked lime and the unreacted coagulant in the return sludge are brought in contact with the waste water for reaction for a long time, by which the unreacted slaked lime and the unreacted coagulant can be utilized more effectively.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2A is a timing chart showing the treatment times in the treatment tanks of the first embodiment when the concentration is normal;

FIG. 3 is a schematic view showing the second embodiment of the waste water treatment equipment of the present invention;

FIG. 4 is a schematic view showing the third embodiment of the waste water treatment equipment of the present invention;

FIG. 7 is a schematic view showing the sixth embodiment of the waste water treatment equipment of the present invention;

FIG. 8A is a timing chart showing the treatment times in the treatment tanks of the sixth embodiment when the concentration is normal;

FIG. 8B is a timing chart showing a treatment time in the treatment tanks of the sixth embodiment when the concentration is low;

FIG. 9 is a schematic view showing the seventh embodiment of the waste water treatment equipment of the present invention;

FIG. 10 is a schematic view showing the eighth embodiment of the waste water treatment equipment of the present invention;

FIG. 11 is a schematic view showing the ninth embodiment of the waste water treatment equipment of the present invention;

FIG. 12 is a schematic view showing the tenth embodiment of the waste water treatment equipment of the present invention;

DETAILED DESCRIPTION OF THE PREFERRED EMBODIMENTS

Figure 1:
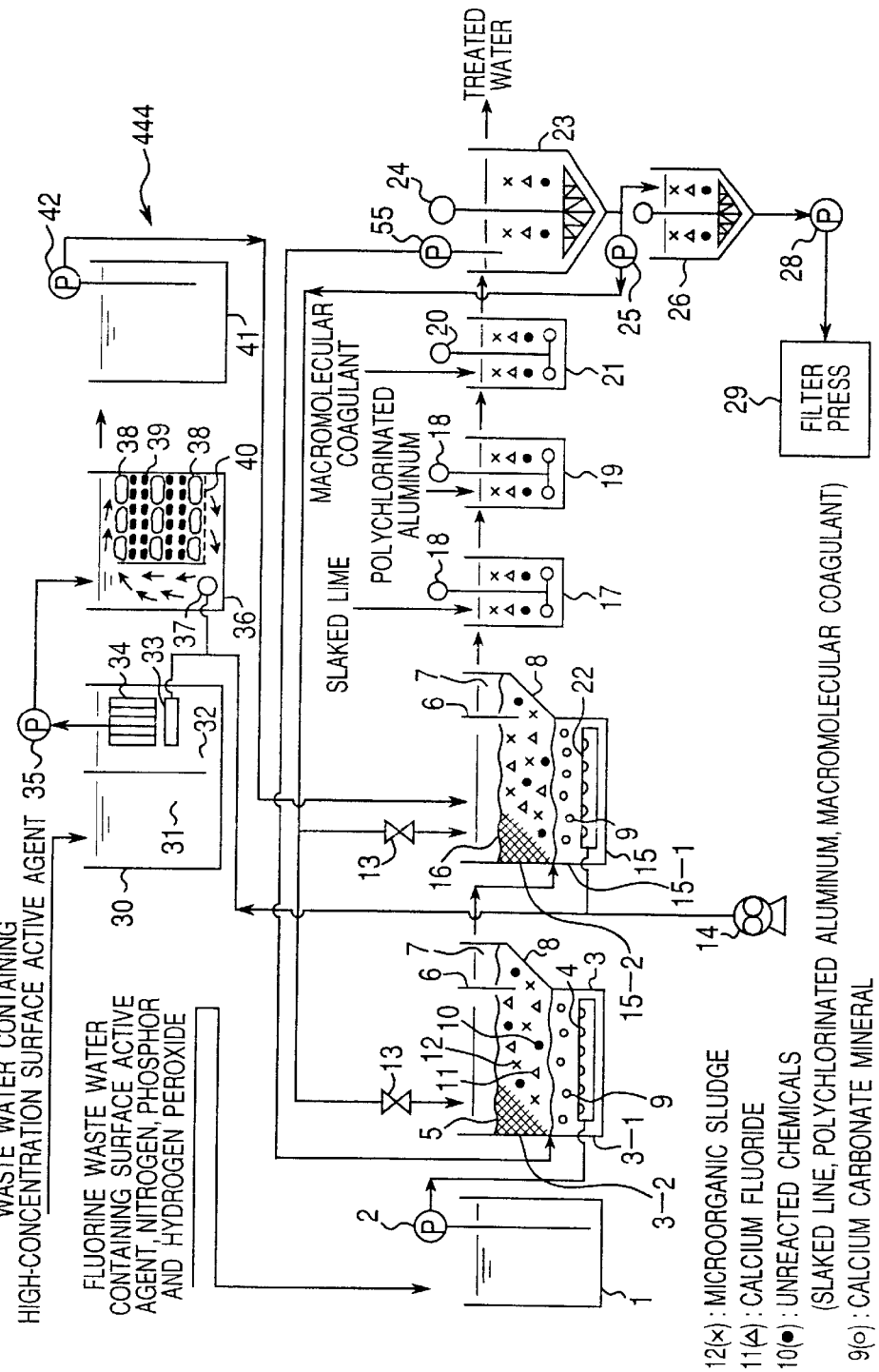
FIG. 1 is a schematic view showing the first embodiment of the waste water treatment equipment of the present invention.

The present invention will be described in detail below on the basis of the embodiments thereof shown in the drawings.

<First Embodiment>

FIG. 1 shows the first embodiment of the waste water treatment equipment of the present invention. This first embodiment is to treat a fluorine waste water containing a surface active agent, nitrogen, phosphor and hydrogen peroxide. This waste water treatment equipment is to reduce the waste by reusing the unreacted slaked lime and coagulant (polychlorinated aluminum and macromolecular coagulant) for treating the waste water.

This waste water treatment equipment is provided with a first water tank 1, a second water tank (anaerobic tank) 3, a third water tank (aerobic tank) 15, a fourth water tank (slaked lime reaction tank) 17, a fifth water tank (polychlorinated aluminum reaction tank) 19, a sixth water tank 21, a seventh water tank (sedimentation tank) 23, an eighth water tank (sludge condensation tank) 26 and a filter press 29.

This waste water treatment equipment has a waste water treatment equipment 444 that serves as waste water treatment equipment of another system for treating a waste water containing a high-concentration surface active agent. This waste water treatment equipment 444 of another system is constructed of a ninth water tank 30, a tenth water tank 36 and an eleventh water tank 41.

The fluorine waste water containing a surface active agent, nitrogen, phosphor and hydrogen peroxide flows from a waste water pipe into the first water tank 1. The fluorine waste water that has flowed into the first water tank 1 is pumped up by a first water tank pump 2 and introduced through a lower inflow pipe 4 into a second water tank lower portion 3-1 of the second water tank 3. The second water tank 3 has the second water tank lower portion 3-1, a second water tank upper portion 3-2 and a separation chamber 7 located adjacent to the second water tank upper portion 3-2 via a partition wall 6.

This second water tank 3 is constructed of the second water tank lower portion 3-1 that has about one half the water level (capacity) of the total capacity of the second water tank 3 and the second water tank upper portion 3-2 that has about one half the water level (capacity) of the total capacity. In the second water tank lower portion 3-1, granular calcium carbonate mineral 9 having a particle diameter of about 0.5 mm is placed in a weak floating state by about 40% to 80% of the capacity of the second water tank lower portion 3-1. This weak floating state means that the granular calcium carbonate mineral 9 is maintained in a flowing state by a water flow generated when the waste water flows inward. In order to achieve this weak floating state, the second water tank lower portion 3-1 has a plurality of lower portion inflow pipes 4 arranged at the bottom thereof. The lower portion inflow pipes 4 are connected to the first water tank pump 2 by way of piping. The water coming from the first water tank pump 2 is discharged through the lower portion inflow pipes 4 so as to maintain the calcium carbonate mineral 9 in the weak floating state.

The calcium carbonate mineral 9 existing in this second water tank lower portion 3-1 can maintain its weak floating state on the condition that the mineral is granular having a particle diameter of about 0.5 mm, the condition that the mineral has a specific gravity of 2.7 and the condition that the mineral is placed in abundance. This weak floating state can be achieved by appropriately controlling the amount of waste water discharged from the lower portion inflow pipes 4. Then, acids such as hydrofluoric acid, sulfuric acid, nitric acid, phosphoric acid included in the fluorine waste water containing a surface active agent, nitrogen, phosphor and hydrogen peroxide introduced by way of the first water tank 1 make calcium ions release from the calcium carbonate mineral 9. The fluorine waste water is generally discharged from the production processes of the semiconductor plant or liquid crystal plant.

In the second water tank upper portion 3-2, an anaerobic sludge zone 5 is formed by the sludge that is precipitated in a seventh water tank (sedimentation tank) 23 and sent back by a sludge return pump 25. If the amount of sludge in this anaerobic sludge zone 5 becomes a specified amount or more, then the height of the anaerobic sludge zone 5 rises, by which the sludge flows out of the separation chamber 7 and enters the third water tank 15. The anaerobic sludge zone 5 is formed on the condition that the second water tank 3 has no aerating means, the condition that the return sludge is a sludge having a good settleability and the condition that the separation chamber 7 is provided adjacent to the second water tank upper portion 3-2. It is to be noted that the reason why the return sludge has a good settleability is that the sludge is generated by a coagulant.

The sludge precipitating in the seventh water tank (sedimentation tank) 23 is the aggregate of the following substances (1) through (5):

(1) calcium fluoride 11 generated through the reaction of the fluorine in the waste water with the calcium carbonate mineral 9;

(2) calcium fluoride 11 generated through the reaction of the slaked lime added to the fourth water tank 17 with the fluorine in the waste water and unreacted slaked lime;

(3) aluminum fluoride generated through the reaction of the polychlorinated aluminum added to the fifth water tank 19 with the fluorine in the waste water, unreacted polychlorinated aluminum and a large amount of hydroxide (aluminum hydroxide) attributed to polychlorinated aluminum;

(4) flocs attributed to the macromolecular coagulant added to the sixth water tank 21 and unreacted macromolecular coagulant; and (5) a microorganic sludge 12 generated through the processes from the second water tank 3 to the seventh water tank 23.

The water level of the waste water in the second water tank 3 is controlled so that the anaerobic sludge zone 5 of the second water tank upper portion 3-2 infallibly sinks. The waste water is thus treated in the second water tank lower portion 3-1, so that the fluorine in the waste water is treated into calcium fluoride (primary treatment of fluorine). Subsequently, in the second water tank upper portion 3-2, the fluorine in the waste water is subjected to coagulation treatment so as to be formed into large flocs of calcium fluoride by the unreacted slaked lime, polychlorinated aluminum and macromolecular coagulant.

The second water tank upper portion 3-2 is anaerobic, and therefore, the nitrate nitrogen in the waste water is reduced by the propagating anaerobic microorganism with a very small quantity of IPA (isopropyl alcohol) and the like used as a hydrogen donor so as to be treated into nitrogen gas. This is expressed by the chemical reaction formula:

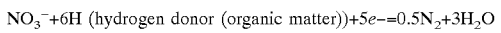

$$NO_3^- + 6H \text{ (hydrogen donor (organic matter))} + 5e^- = 0.5N_2 + 3H_2O$$

The hydrogen peroxide that serves as the oxidizing agent in the waste water is treated into water and oxygen gas by the reducibility owned by the anaerobic microorganism propagating in the second water tank upper portion 3-2.

The unreacted slaked lime included in the return sludge exists in the second water tank upper portion 3-2, and therefore, the phosphor in the waste water somewhat is treated by reacting with the slaked lime (calcium hydroxide) to become calcium phosphate. However, this reaction is a weak reaction attributed to the stirring by only the water flow.

The bottom surface of the second water tank lower portion 3-1 is provided with an inclined surface 8, and this inclined surface 8 is upwardly aslant toward the end wall from the region where the lower portion inflow pipes 4 are arranged in the lower region of the separation chamber 7. This inclined surface 8 is provided with no lower portion inflow pipe. Therefore, the calcium carbonate mineral 9 descends along the inclined surface 8 in the separation chamber 7, by which the calcium carbonate mineral 9 is prevented from flowing out of the separation chamber 7.

On the other hand, the calcium fluoride 11 in the floc form having a small specific gravity and the microorganic sludge 12 eventually flow out of the separation chamber 7, whereas the calcium carbonate mineral 9 that serves as a fluorine treating material does not flow out of the separation chamber 7 of the second water tank 3 to the outside.

The waste water treated in the second water tank (anaerobic tank) 3 flows into the third water tank (aerobic tank) 15. The third water tank 15 is constructed of a third water tank lower portion 15-1, a third water tank upper portion 15-2 and a separation chamber 7 located adjacent to the third water tank upper portion 15-2. Into the third water tank 15 is introduced a treated water (treated water that contains a microorganism having excellent surface active agent biodegradability) obtained by biologically treating a waste water containing a high-concentration surface active agent by the waste water treatment equipment 444 of another system.

The purpose of introducing the treated water that contains the microorganism having excellent surface active agent biodegradability into the third water tank 15 will be described below.

The waste water from the second water tank 3 flowing into the third water tank 15 contains the surface active agent and microorganism, however, the surface active agent is not easily biologically decomposed by the microorganism. That is, among various sorts of surface active agents used in the field of IC industry, many surface active agents, inclusive of the lately developed surface active agents, have poor biodegradability.

Therefore, the microorganism having the excellent surface active agent degradability is cultured and propagated in the waste water treatment equipment 444 of another system, mixed in the treated water and then introduced into the third water tank upper portion 15-2 by an eleventh water tank pump 42.

The waste water treatment equipment 444 of the waste water containing a high-concentration surface active agent of another system will be described below. In an IC plant, there is existing a waste water containing a developing solution as a waste water containing a high-concentration surface active agent. When biologically treating this waste water containing a developing solution, in general, effervescence due to the surface active agent in the aeration tank often emerges as a problem. However, in the ninth water tank 30 constructed of an anaerobic section 31 and an aerobic section 32, by increasing the microorganic concentration in the ninth water tank 30 utilizing a separation membrane 34, the developing solution component and the surface active agent in the waste water containing a developing solution can be treated while suffering less influence from the effervescence of the surface active agent.

The microorganic concentration in the ninth water tank 30 is not lower than 10000 ppm in terms of MLSS (Mixed Liquor Suspended Solid).

The surface active agent that is easily decomposed is biologically decomposed in the ninth water tank 30. The surface active agent that has not been biologically decomposed in the ninth water tank 30 is introduced into the tenth water tank 36 by a separation membrane use pump 35. The tenth water tank 36 is filled with activated carbon bags 38 in which activated carbon is stored and Bincho charcoal pieces 39. The slightly-soluble surface active agent in the waste water that has passed through the separation membrane 34 is adsorbed by the activated carbon in the activated carbon bags 38 and the Bincho charcoal pieces 39 and thereafter treated by the microorganism that is fixed and propagated on the surfaces of the activated carbon and the Bincho charcoal pieces 39.

Then, as time elapses, the microorganism that is fixed and propagated on the surfaces of the activated carbon and the Bincho charcoal pieces 39 becomes a microorganism that can biologically decompose the slightly-soluble surface active agent and further propagated to come into existence not only on the surfaces of the activated carbon and the Bincho charcoal pieces 39 but also in the water.

The microorganism that is propagating to exist even in the water and the treated water in the tenth water tank 36 flow into the eleventh water tank 41 in an overflow (natural downflow) manner. The treated water that contains the microorganism capable of biologically decomposing the slightly-soluble surface active agent and is reserved for a specified time after flowing into the eleventh water tank 41 is introduced into the third water tank upper portion 15-2 by the pump 42 provided for the eleventh water tank 41.

The sludge precipitated in the seventh water tank (sedimentation tank) 23 is sent back to the third water tank upper portion 15-2 by the sedimentation tank sludge return pump 25 and forms an aerobic sludge zone 16. It is to be noted that the sludge precipitated in the seventh water tank (sedimentation tank) 23 is quite the same as the sludge that is sent back to the second water tank (anaerobic tank) 3, as described hereinabove. If the amount of sludge in the aerobic sludge zone 16 becomes equal to or greater than a specified amount, then the height of the aerobic sludge zone 16 rises to flow the sludge out of the separation chamber 7 into the fourth water tank 17.

Because of the aeration from a blower 14 and an air diffusion pipe 22 in the third water tank (aerobic tank) 15, the return sludge having a good settleability to the third water tank (aerobic tank) 15 and the separation chamber 7 provided adjacent to the third water tank upper portion 15-2, the aerobic sludge zone 16 is formed in the third water tank upper portion 15-2. The reason why the return sludge has a good settleability is that the sludge is formed by a coagulant. In the aerobic sludge zone 16 of this third water tank upper portion 15-2, the waste water initially has weak acidity, pneumatic stirring and a sufficient retention time, and therefore, the sludge is easily loosened by air to assure the regeneration thereof.

On the other hand, the calcium carbonate mineral 9 is placed in the third water tank lower portion 15-1. The third water tank lower portion 15-1 is provided with an air diffusion pipe 22, and aeration air is discharged from this air diffusion pipe 22 to pneumatically stir the inside of the third water tank 15. By this operation, the placed calcium carbonate mineral 9 is maintained in a state in which the mineral is ready for reaction in a flowing state due to the pneumatic stirring. In the third water tank 15, the calcium fluoride 11, microorganic sludge 12 and unreacted chemicals (unreacted slaked lime, polychlorinated aluminum and macromolecular coagulant) 10 that have flowed from the second water tank 3 are maintained in a state in which the above substances are ready for reaction in a flowing state due to the pneumatic stirring. The calcium fluoride 11, microorganic sludge 12 and unreacted chemicals 10 are also contained in the return sludge from the seventh water tank 23. It is to be noted that the air diffusion pipe 22 is connected to the blower 14 by way of an air pipe. For the blower 14, a Roots blower that is generally produced and put on the market was selected.

Figure 14:
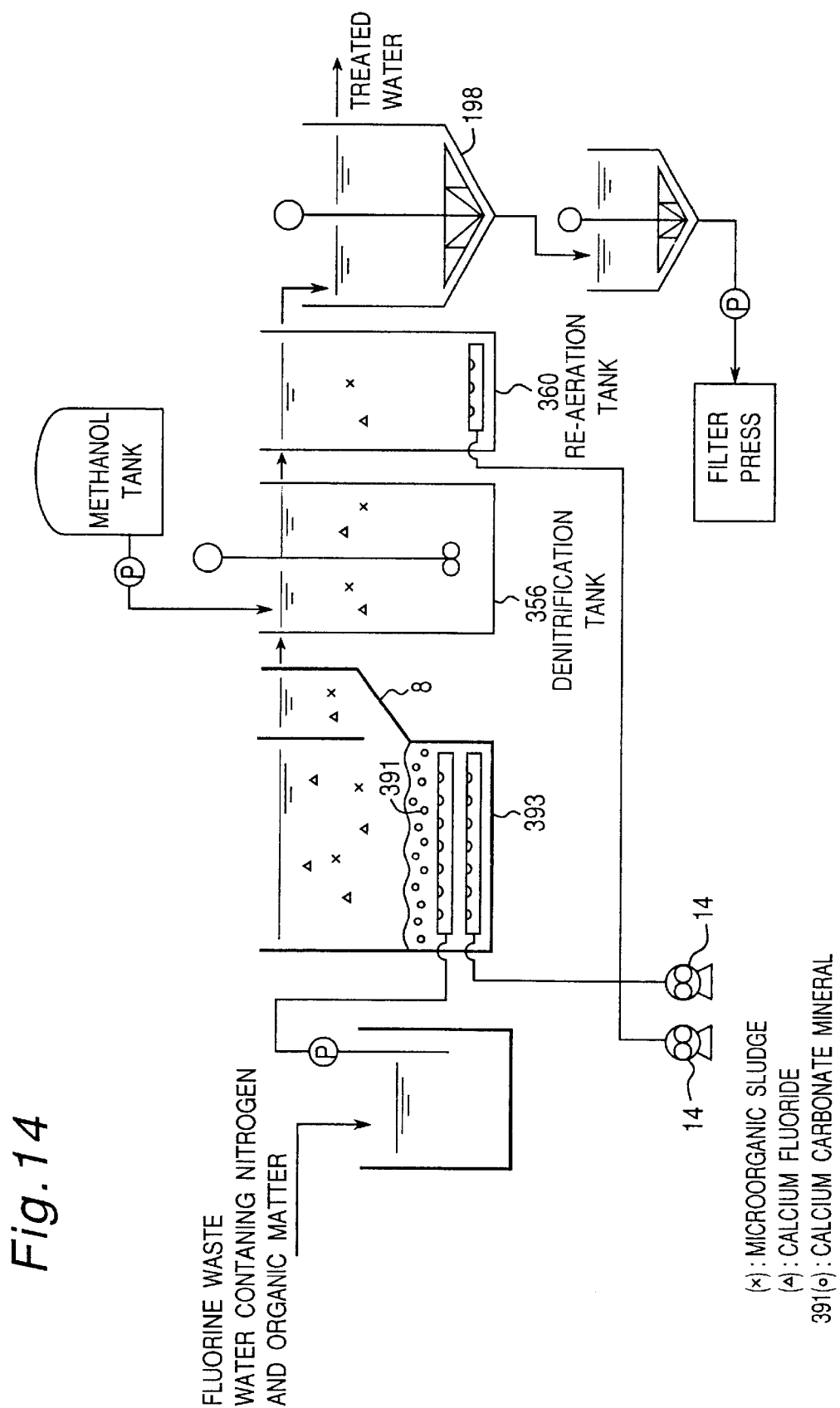
FIG. 14 is a view showing waste water treatment equipment as a comparative example for treating a fluorine waste water containing nitrogen and organic matter.
Figure 15:
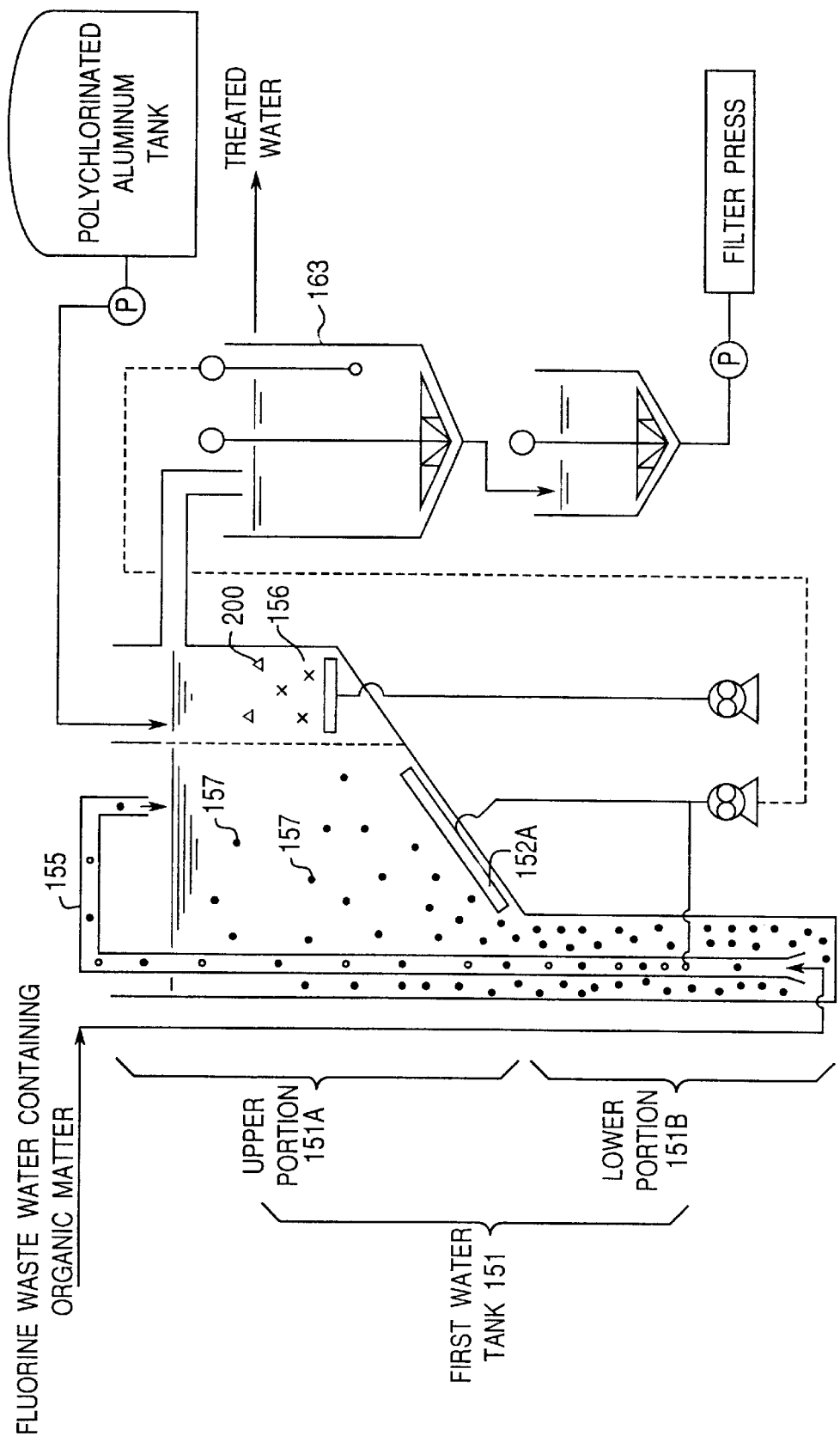
FIG. 15 is a view showing waste water treatment equipment of another prior art example for treating a fluorine waste water containing organic matter.
Figure 16:
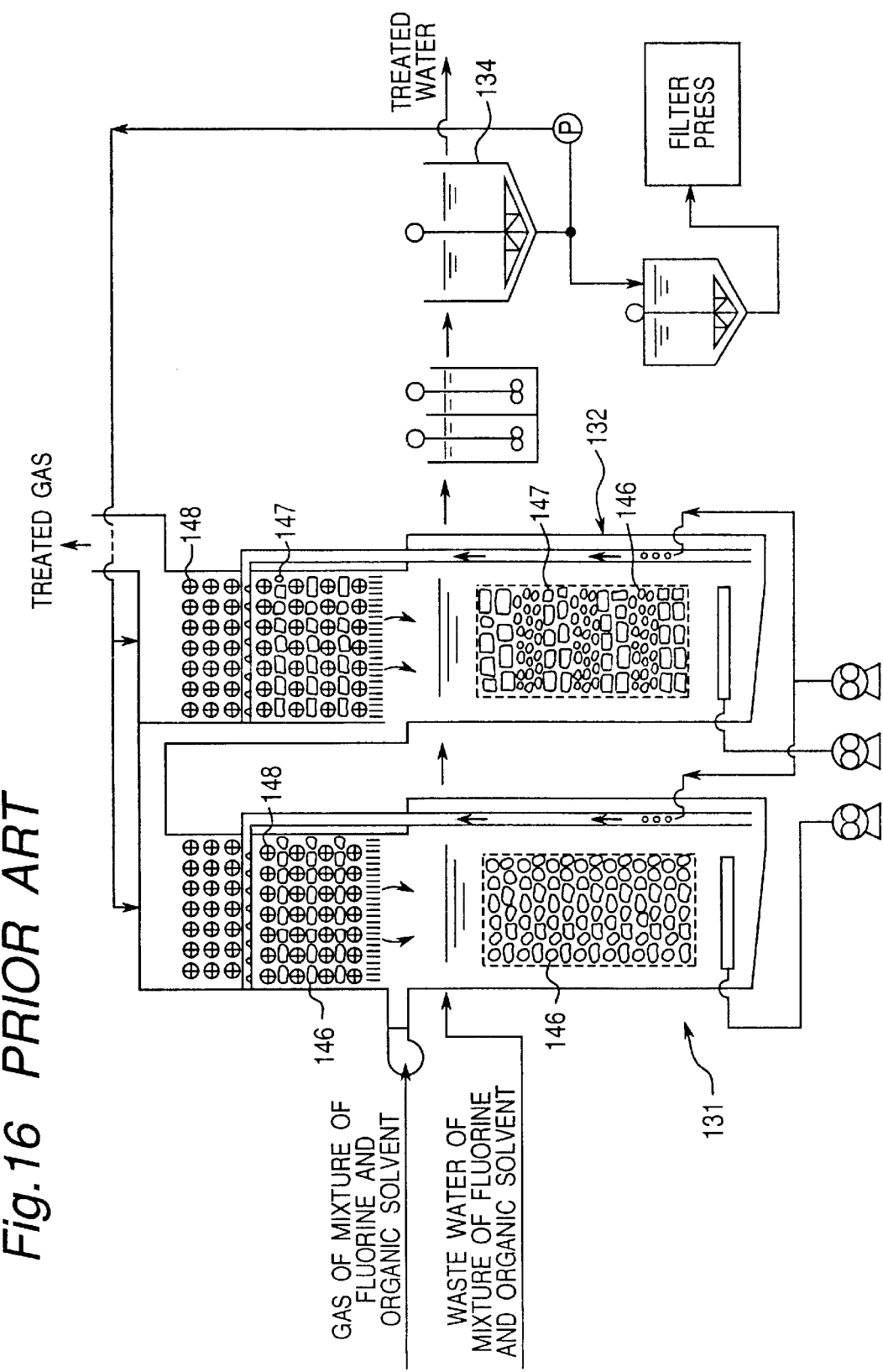
FIG. 16 is a view showing waste water treatment equipment of another prior art example for treating waste water of a mixture of fluorine and organic solvent as well as exhaust gas of a mixture of fluorine and organic solvent according to a fixed system.

According to the practical example of implementation, if the calcium carbonate mineral 9 having a particle diameter of 0.5 mm is adopted, then the air flow rate of the blower 14 per volume of 1 $m^3$ of the third water tank 15 is set to 30 to 60 ($m^3$/day). This air flow rate is about one half the air flow rate per unit volume of the conventional system in which only the calcium carbonate mineral is used according to the comparative example shown in FIG. 14 and is about one half the air flow rate of the conventional system in which only the calcium carbonate mineral is used according to the comparative example shown in FIG. 17, the comparative examples being described later. It is to be noted that a second water tank 393 shown in FIG. 14 is an aerobic tank similar to the second water tank 193 of the eighth prior art example (FIG. 18).

Thus, by the weak air blown from the air diffusion pipe 22, the aerobic sludge zone 16 of the third water tank upper portion 15-2 and the third water tank lower portion 15-1 enter into a weak floating state, and the waste water flows into a portion (portion around the middle portion of the third water tank 15) at the boundary between the third water tank upper portion 15-2 and the third water tank lower portion 15-1. Then, the fluorine in the waste water reacts with the calcium carbonate mineral 9, the unreacted slaked lime and the unreacted coagulant, thereby forming the flocs of calcium fluoride 11. By this operation, the tertiary treatment of fluorine is executed to treat the waste water. It is to be noted that the primary treatment is executed in the second water tank lower portion 3-1 and the secondary treatment is executed in the second water tank upper portion 3-2.

The reactions occurring in the third water tank 15 are enumerated by the following items (1) through (5).

(1) Through the tertiary treatment of fluorine, the fluorine in the waste water reacts with the calcium carbonate mineral 9 and the unreacted slaked lime to form the flocs of the calcium fluoride 11.

(2) The flocs of the calcium fluoride 11 generated through the tertiary treatment become large shaped flocs having a good settleability by the unreacted polychlorinated aluminum and the unreacted macromolecular coagulant.

(3) The organic matter such as the surface active agent in the waste water is biologically treated by coming in contact with the microorganism in the high-concentration microorganic sludge by pneumatic stirring.

(4) Ammoniacal nitrogen and nitrite nitrogen are oxidized by air to become nitrate nitrogen.

(5) The phosphor in the waste water reacts with the unreacted slaked lime to become calcium phosphate and is formed into large flocs by the unreacted coagulant.

It is preferable to design the second water tank (anaerobic tank) 3 and the third water tank (aerobic tank) so that the waste water treated in the third water tank 15 becomes neutral at the exit of the separation chamber 7. Specifically, when pH of the waste water is not greater than three, it is preferable to design each of the second water tank 3 and the third water tank 15 so that the retention time of the waste water is set to two hours or longer, also depending on the amount of unreacted chemicals in the return sludge. That is, the total retention time in the second water tank 3 and the third water tank 15 becomes four hours.

The fluorine in the waste water has already undergone the primary treatment and the secondary treatment in the second water tank 3, and therefore, no specific problem occurs even if the third water tank 15 has an aeration air rate of about 50 cubic meters a day per cubic meter of the volume thereof.

As a result, in the waste water treatment equipment operated at the aeration air rate of about 50 cubic meters a day per cubic meter of the volume of the third water tank 15, the specified fluorine removal ratio can be secured and the aeration air rate is reduced by half as compared with that of the conventional system. Accordingly, this can facilitate energy saving in terms of electric power. The comparison provided here is the comparison of the number of blowers with respect to the conventional systems of the comparative examples shown in FIG. 14 and FIG. 17.

The bottom surface of the third water tank lower portion 15-1 is provided with an inclined surface 8, and this inclined surface 8 is upwardly aslant toward the end wall from the region where the air diffusion pipe 22 is arranged in the lower region of the separation chamber 7. This inclined surface 8 is provided with no air diffusion pipe. With this arrangement, the calcium carbonate mineral 9 descends along the inclined surface 8 in the separation chamber 7, thereby preventing the calcium carbonate mineral 9 from flowing out of the separation chamber 7. On the other hand, the calcium fluoride 11 in the floc form having a small specific gravity and the microorganic sludge 12 eventually flow out of the separation chamber 7, whereas the calcium carbonate mineral 9 that serves as a fluorine treating material does not flow out of the separation chamber 7 of the third water tank 15 to the outside.

As described above, in the waste water that has flowed from the second water tank 3 into the middle portion of the third water tank 15 (at the boundary between the third water tank lower portion 15-1 and the third water tank upper portion 15-2), the fluorine in the waste water reacts with the calcium carbonate mineral 9 that is weakly flowing at this boundary, thereby treating the fluorine concentration in the waste water to about 15 ppm and making the waste water pH approach six. That is, the tertiary treatment of fluorine is executed. Further, the waste water introduced into the aerobic sludge zone 16 of the third water tank upper portion 15-2 is mixed and stirred with the return sludge that includes the unreacted slaked lime, unreacted polychlorinated aluminum, unreacted macromolecular coagulant and microorganism. Therefore, in this third water tank upper portion 15-2, the following treatment processes (1), (2) and (3) are executed.

(1) The fluorine (15 ppm) in the waste water obtained after the tertiary treatment of fluorine reacts with the unreacted slaked lime in the return sludge to become the calcium fluoride 11, and the fluorine concentration in the waste water is further reduced to a concentration of not greater than 10 ppm by the unreacted coagulant. This serves as a quaternary treatment, and pH comes closer to the neutrality.

(2) The surface active agent in the waste water is biologically treated by the high-concentration aerobic microorganism in the aerobic sludge zone 16. This high-concentration aerobic microorganism in the aerobic sludge zone 16 includes the microorganism capable of biologically decomposing the slightly-soluble surface active agent that has existed in the waste water treatment equipment 444 of another system, and therefore, the surface active agent in the waste water can be efficiently treated.

(c) The phosphor in the waste water is treated through the reaction with the unreacted slaked lime in the return sludge to become calcium phosphate. This serves as the secondary treatment of phosphor.

The waste water of which the fluorine, surface active agent, phosphor and hydrogen peroxide have been treated (i.e., the water to be treated) is introduced into the fourth water tank (slaked lime reaction tank) 17. Specifically, the waste water treated in the third water tank 15 is conveyed to the fourth water tank 17 by way of an outflow pipe (not shown) provided in a position above the separation chamber 7 of the third water tank 15.

In this fourth water tank 17, slaked lime is added and the waste water and the slaked lime are rapidly stirred by a rapid stirrer 18. By this operation, the phosphor in the waste water is further treated to become calcium phosphate. This becomes the tertiary treatment of phosphor. The primary treatment of phosphor is the reaction treatment with the unreacted slaked lime in the second water tank upper portion 3-2. The secondary treatment of phosphor is the reaction treatment with the unreacted slaked lime in the third water tank upper portion 15-2. The calcium phosphate in the waste water is eventually treated by being precipitated in the seventh water tank (sedimentation tank) 23.

The slaked lime is added to the fourth water tank 17, and therefore, the fluorine in the waste water is further highly treated. This is the quinary treatment of fluorine.

According to the result of operation of the actual equipment, the phosphor in the waste water does not react with the calcium released from the calcium carbonate mineral 9. Therefore, the phosphor can scarcely be treated in the second water tank lower portion 3-1 and the third water tank lower portion 15-1.

Next, the waste water is introduced into the fifth water tank (polychlorinated aluminum reaction tank) 19. In this fifth water tank 19, an aluminum agent (polychlorinated aluminum) is added as a coagulant for the formation of the cores of flocs, and the waste water and the polychlorinated aluminum are rapidly stirred by the rapid stirrer 18, forming minute flocs.

Next, the waste water is introduced from the fifth water tank 19 into the sixth water tank 21. In this sixth water tank 21, a macromolecular coagulant is added so as to enlarge the flocs. This macromolecular coagulant has a greater effect as the waste water comes closer to the neutrality, and the fluorine and phosphor can be efficiently removed from the waste water.

The waste water that has undergone the treatment in the sixth water tank 21 is then conveyed to the seventh water tank 23. This seventh water tank 23 is provided with a clarifier 24 and executes the same treatment as that of the general sedimentation tank. That is, in this seventh water tank 23, the solid matter is precipitated and thereafter scraped up by the clarifier 24 so as to be collected to the center in the lower region of the seventh water tank (sedimentation tank) 23, while the supernatant liquid in the upper portion becomes the treated water.

Above the seventh water tank 23 is provided a circulation pump 55 that introduces the supernatant liquid into the boundary between the second water tank upper portion 3-2 and the second water tank lower portion 3-1. This is intended for introducing the nitrate nitrogen that exists in the supernatant liquid into the anaerobic sludge zone 5 and denitrifying (treating the nitrogen of) the same. Then, an eighth water tank 26 that is the general sludge condensation tank receives the sludge that has been scraped up in the seventh water tank 23 serving as the sedimentation tank and is introduced through the lower portion of the seventh water tank 23 and condenses the sludge. Then, the condensed sludge is conveyed to the filter press 29 that serves as a dehydrator.

Figure 2B:
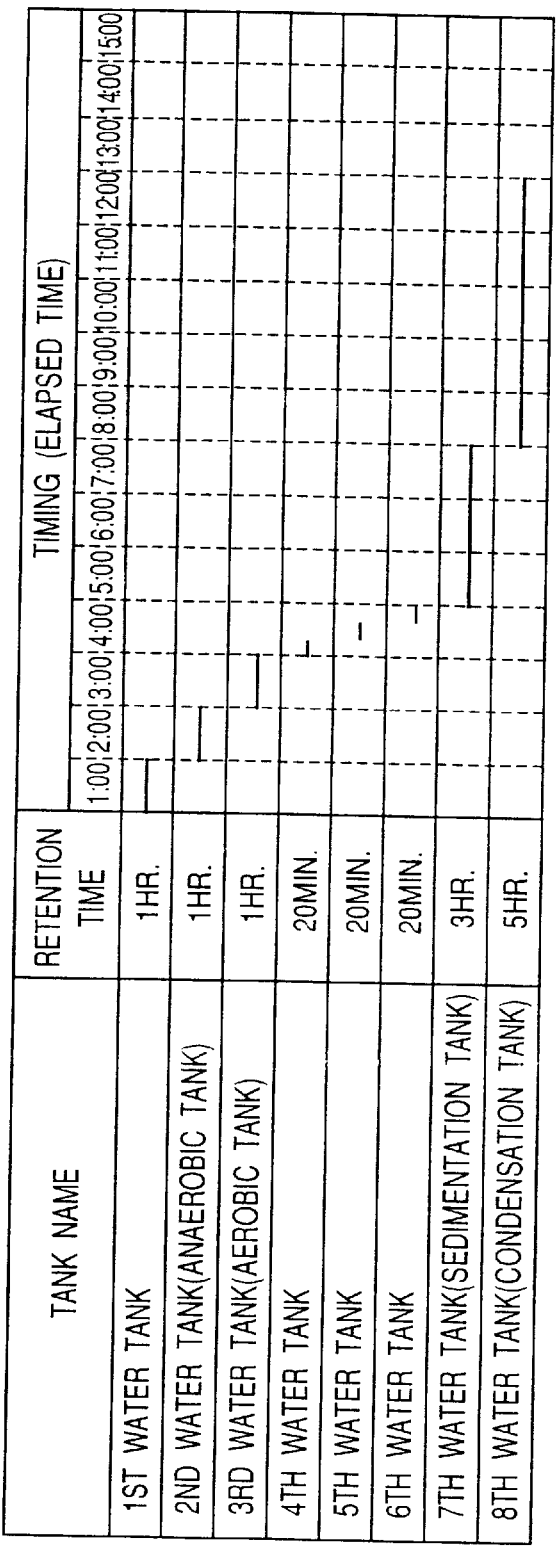
FIG. 2B is a timing chart showing the treatment times in the treatment tanks of the first embodiment when the concentration is low.

In this first embodiment, if the waste water has the normal concentration, as shown in FIG. 2A, then the retention time of the waste water is made totally not shorter than four hours comprised of the retention time of two hours in the second water tank 3 and the retention time of two hours in the third water tank 15. However, the reaction time in each of the fourth water tank 17, the fifth water tank 19 and the sixth water tank 21 is allowed to be about 20 minutes or 15 minutes. In the case where the waste water has a low concentration, as shown in FIG. 2B, the retention time of the waste water is made totally not shorter than two hours comprised of the retention time of one hour in the second water tank 3 and the retention time of one hour in the third water tank 15. However, the reaction time in each of the fourth water tank 17, the fifth water tank 19 and the sixth water tank 21 is allowed to be about 20 minutes or 15 minutes.

Although the particle diameter of the granular calcium carbonate mineral 9 is set to about 0.5 mm in the first embodiment, it is proper to set this particle diameter within a range of 0.1 mm to 2 mm.

Figure 17:
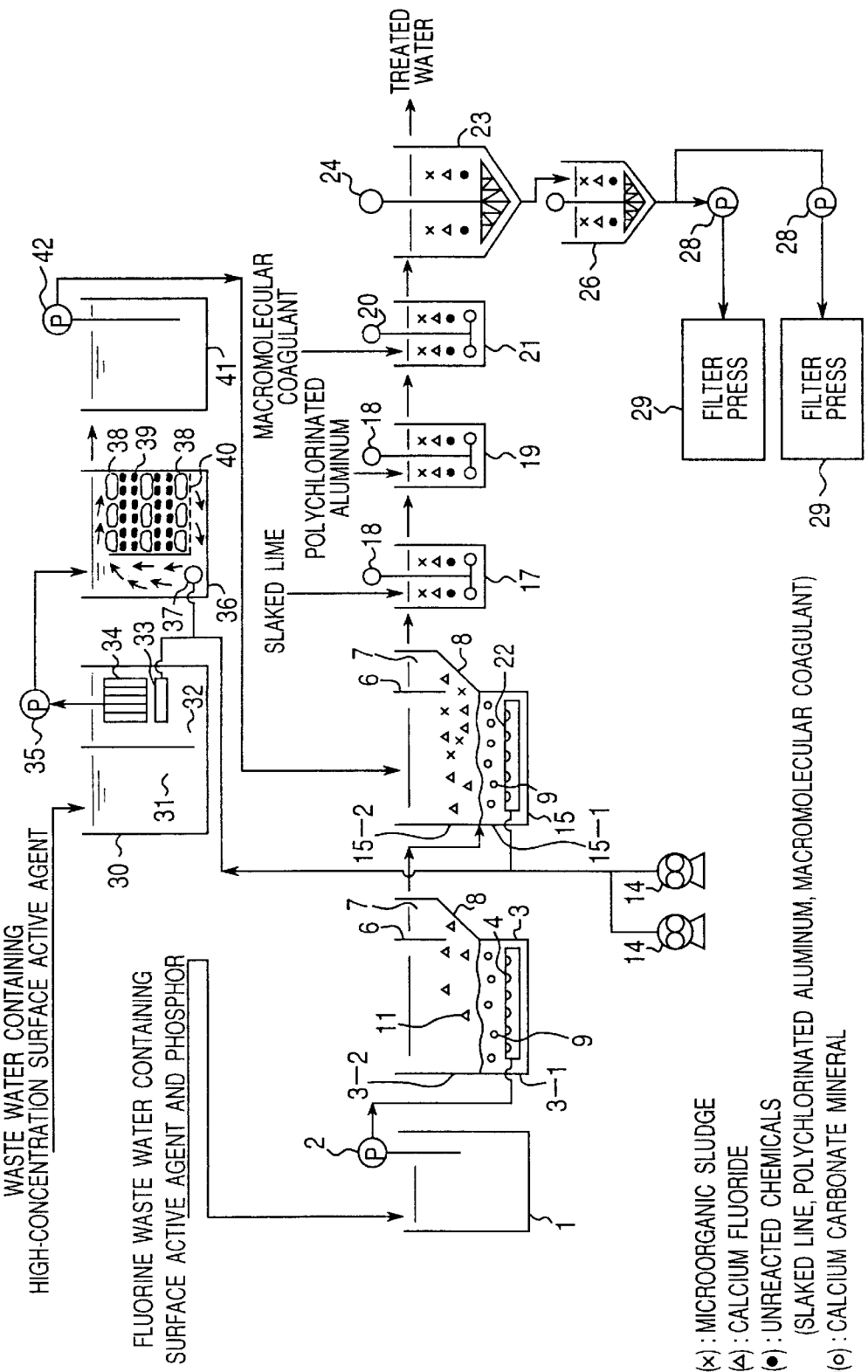
FIG. 17 is a view showing waste water treatment equipment as a comparative example for treating fluorine waste water containing a surface active agent, nitrogen, phosphor and hydrogen peroxide.
Figure 18:
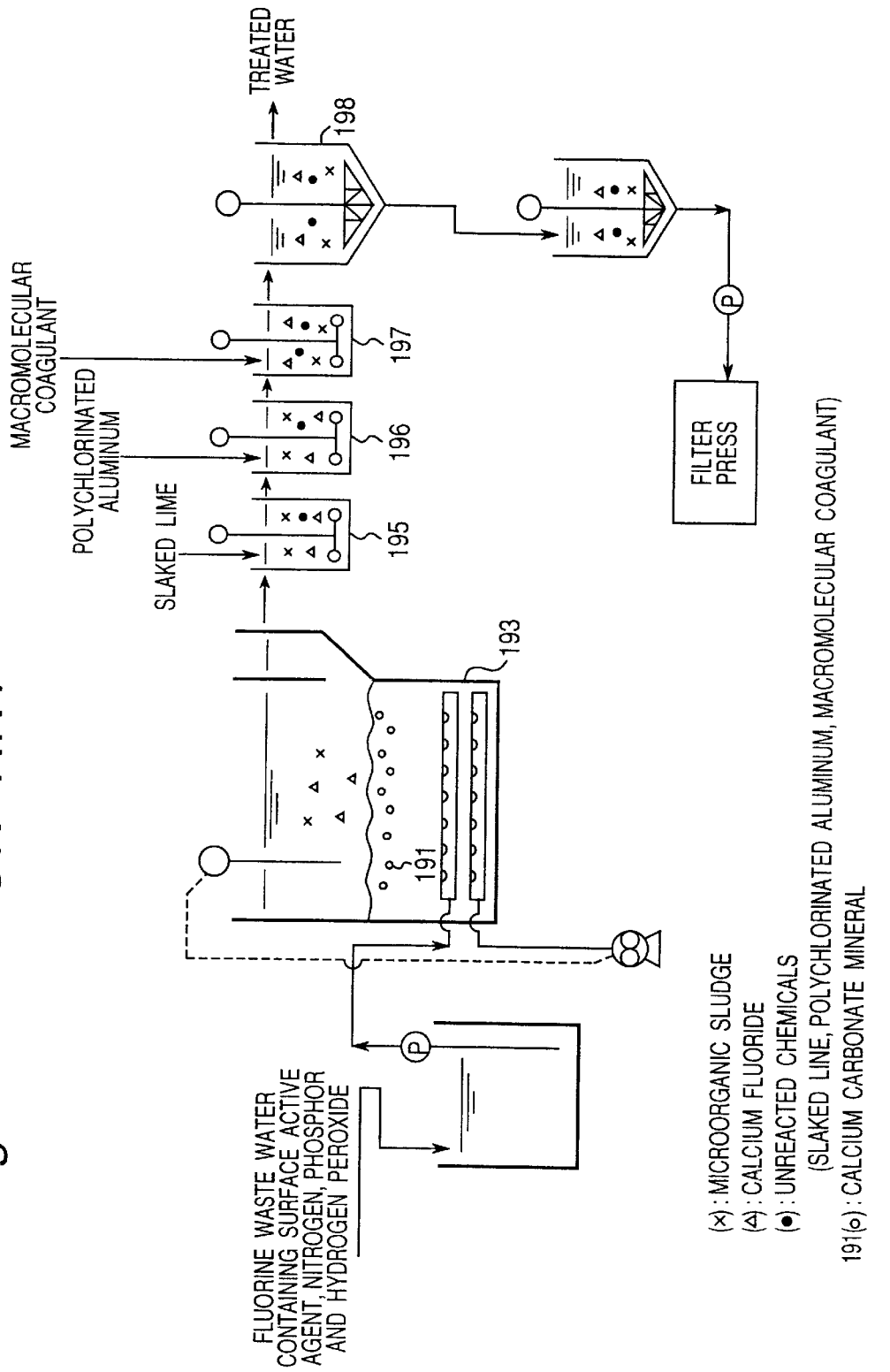
FIG. 18 is a view showing the construction of a prior art example.

FIG. 17 shows an example to be compared with the first embodiment. This comparative example is the conventional system. In this comparative example, the sludge from the seventh water tank 23 is sent back to neither the second water tank 3 nor the third water tank 15, and neither of the anaerobic sludge zone 5 nor the aerobic sludge zone 16 is formed. As shown in FIG. 17, in this comparative example, the sedimentation tank sludge return pump 25 and the piping of the first embodiment are eliminated. Furthermore, in this comparative example, two blowers 14 are provided for maintaining the pH value at and around seven in the third water tank upper portion 15-2.

Therefore, if the first embodiment of FIG. 1 is compared with the comparative example shown in FIG. 17, then the first embodiment has the smaller amount of operating blowers 14, meaning that the amount of air necessary for the third water tank 15, i.e., the amount of air discharged from the blower 14 can be made about one half that of the comparative example according to the first embodiment. Therefore, the cost for the electric power can be reduced by half to allow energy-saving type waste water treatment equipment to be provided.

The amount of air that is discharged from the blower 14 and supplied to the ninth water tank 30 and the tenth water tank 36 is made equal in the first embodiment and the comparative example. The comparative example shown in FIG. 17 is provided with no sludge return equipment from the seventh water tank 23 and the eighth water tank 26 to the second water tank upper portion 3-2 and the third water tank upper portion 15-2. Therefore, the unreacted slaked lime, unreacted polychlorinated aluminum and unreacted macromolecular coagulant are subjected to dehydrating treatment by two filter press units 29 and 29 without being reused. Therefore, the unreacted slaked lime, unreacted polychlorinated aluminum and unreacted macromolecular coagulant are included in the sludge, and accordingly, there is a large amount of sludge as a waste.

In contrast to this, according to the first embodiment shown in FIG. 1, the unreacted slaked lime, unreacted polychlorinated aluminum and unreacted macromolecular coagulant are sent back to the second water tank upper portion 3-2 and the third water tank upper portion 15-2 so as to be reused, and therefore, the amount of sludge that serves as the waste dehydrated by the filter press 29 is remarkably reduced in amount. Therefore, in the first embodiment of FIG. 1, the treatment can be achieved by only one filter press 29 differently from the comparative example of FIG. 17.

Another reason for the reduction in amount of the sludge in the first embodiment of FIG. 1, in comparison with the comparative example, is that the aeration is executed on condition that the return sludge exists in the third water tank (aerobic tank) 15 and the retention time of the waste water is not shorter than two hours. With this arrangement, the components in the sludge are dissolved into the waste water, and practically, the amount of sludge is reduced while being released as ions such as calcium ions. For instance, assuming that the calcium sulfate exists as a precipitate or sludge, then the calcium sulfate is dissolved by aeration in the form of sulfate ions and calcium ions into the waste water, as a consequence of which the solid matter reduces in amount.

It is to be noted that the calcium fluoride 11 that is generated after the reaction of the fluorine treatment is slightly-soluble, and therefore, the calcium fluoride does not dissolve at all by aeration. The aeration process in this third water tank 15 is intended firstly for reducing the amount of sludge by leaving only the slightly-soluble calcium fluoride 11 and dissolving the other components to the respective degrees of dissolution of the components and secondly for maintaining the stirring and the propagation of the aerobic microorganism inside the third water tank 15.

<Second Embodiment>

Next, FIG. 3 shows the second embodiment of the waste water treatment equipment of the present invention. In this second embodiment, same reference numerals are given to the same components as those of the aforementioned first embodiment and the points different from those of the first embodiment will be preponderantly described.

This second embodiment differs from the first embodiment only in the following points (1) and (2).

(1) The equipment for sending the sludge precipitated in the seventh water tank 23 back to the second water tank 3 and the third water tank 15 by the sedimentation tank sludge return pump 25 is eliminated.

(2) The sludge condensed in the eighth water tank 26 is sent back to the second water tank upper portion 3-2 and the third water tank upper portion 15-2 by a condensation tank pump 27.

In this second embodiment, the sludge condensed in the eighth water tank 26 is sent back to the second water tank upper portion 3-2 and the third water tank upper portion 15-2 by the condensation tank pump 27. Therefore, the sludge concentrations in the anaerobic sludge zone 5 of the second water tank upper portion 3-2 and the aerobic sludge zone 16 of the third water tank upper portion 15-2 easily increase as compared with those of the first embodiment, by which the waste water treatment efficiency of the objective substance to be treated increases. In particular, the sludge that has been condensed for a long time (about five hours) in the anaerobic state in the eighth water tank (condensation tank) 26 is sent back. Therefore, the sludge concentration increases in the anaerobic sludge zone 5 and the oxygen in the waste water is rapidly consumed. Consequently, the anaerobic property is promoted to further propagate the anaerobic microorganism, by which the biodegradability of the hydrogen peroxide in the waste water is significantly improved.

The supernatant liquid including the nitrate nitrogen from the seventh water tank 23 is introduced into the lower portion of the anaerobic sludge zone 5 where the anaerobic property is promoted, and therefore, the denitrification efficiency is improved further than in the first embodiment. Furthermore, the microorganic concentration increases in both the anaerobic sludge zone 5 and the aerobic sludge zone 16, and therefore, the treatment performance of the surface active agent, or the objective substance to be treated in the waste water is also improved.

<Third Embodiment>

Next, FIG. 4 shows the waste water treatment equipment of the third embodiment of the present invention. The waste water treatment equipment of this third embodiment differs from the aforementioned first embodiment only in the following point (1). Therefore, same reference numerals are given to the same components as those of the first embodiment and no detailed description is provided for them.

(1) The sludge condensed in the eighth water tank 26 is sent back to the second water tank upper portion 3-2 and the third water tank upper portion 15-2 by the condensation tank sludge return pump 27.

In this third embodiment, both the sludge precipitated in the seventh water tank 23 and the sludge condensed in the eighth water tank 26 can be sent back to the second water tank upper portion 3-2 and the third water tank upper portion 15-2. Therefore, the rate of circulation of the sludge from the second water tank upper portion 3-2 to the eighth water tank 26 is increased, so that the contact catalytic reaction of the unreacted slaked lime and unreacted coagulant included in the sludge with the waste water can be easily promoted.

<Fourth Embodiment>

Figure 5:
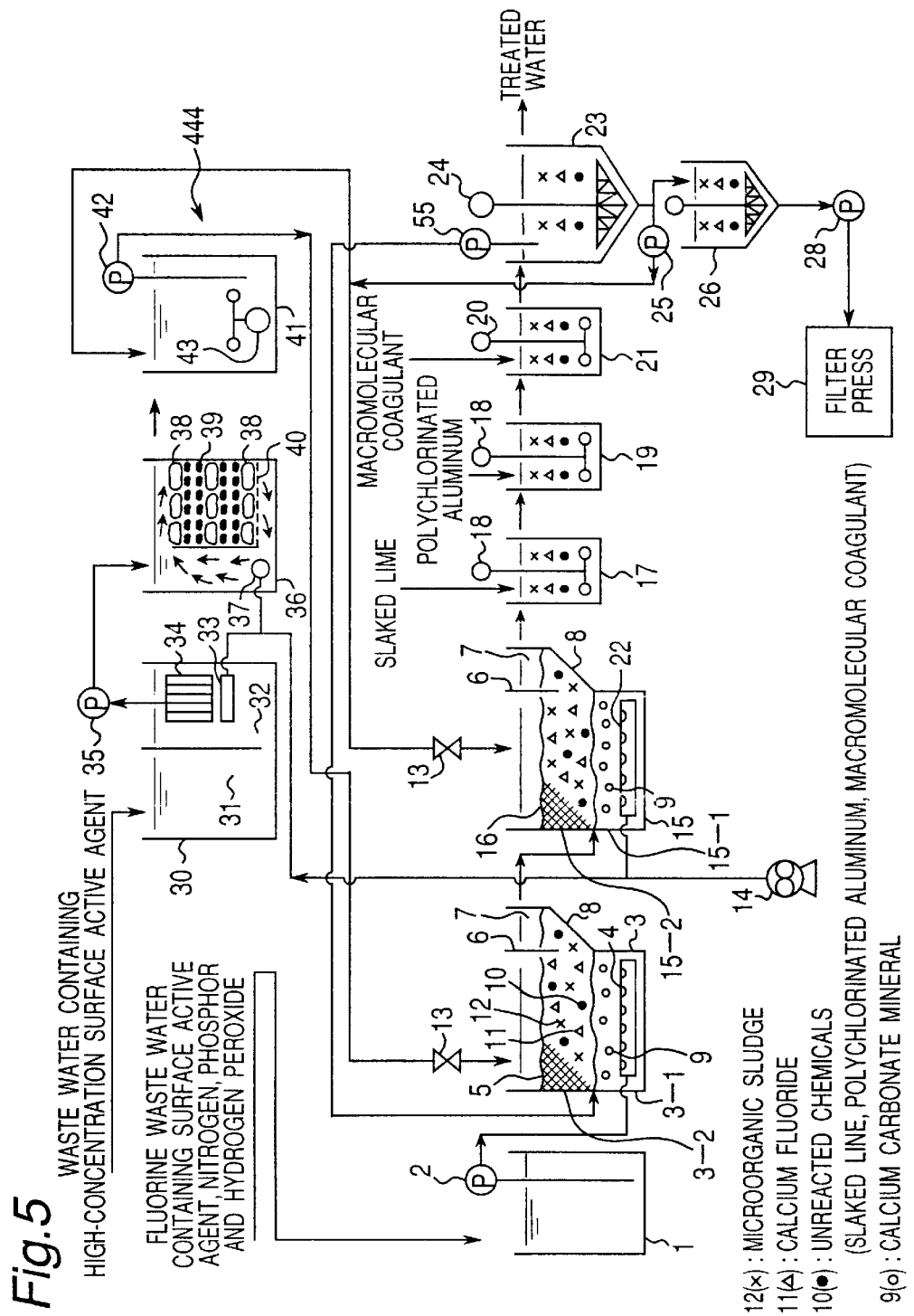
FIG. 5 is a schematic view showing the fourth embodiment of the waste water treatment equipment of the present invention.

Next, FIG. 5 shows the waste water treatment equipment of the fourth embodiment of the present invention. The waste water treatment equipment of this fourth embodiment differs from the aforementioned first embodiment only in the following points (1), (2) and (3). Therefore, same reference numerals are given to the same components as those of the first embodiment and no detailed description is provided for them.

(1) The sludge precipitated in the seventh water tank 23 is sent back to the third water tank upper portion 15-2 and the eleventh water tank 41 by the sludge return pump 25 and not sent back to the second water tank upper portion 3-2.

(2) An underwater stirrer 43 capable of executing stirring under anaerobic conditions is provided.

(3) The sludge water including the sludge from the eleventh water tank 41 is introduced into the second water tank upper portion 3-2 instead of the third water tank upper portion 15-2.

Therefore, in this fourth embodiment, the sludge precipitated in the seventh water tank 23 can be introduced into the eleventh water tank 41, and the anaerobic microorganism can be bred in the eleventh water tank 41 under anaerobic conditions. The microorganism capable of biologically decomposing the slightly-soluble surface active agent introduced from inside the tenth water tank 30 into the eleventh water tank 41 can be fixed and propagated in the introduced sludge over time. Then, the sludge water including the anaerobic microorganism bred in the eleventh water tank 41 is introduced into the second water tank upper portion 3-2. As a result, the treatment efficiency of the slightly-soluble surface active agent in the waste water is improved in the second water tank 3 as compared with the first embodiment.

<Fifth Embodiment>

Figure 6:
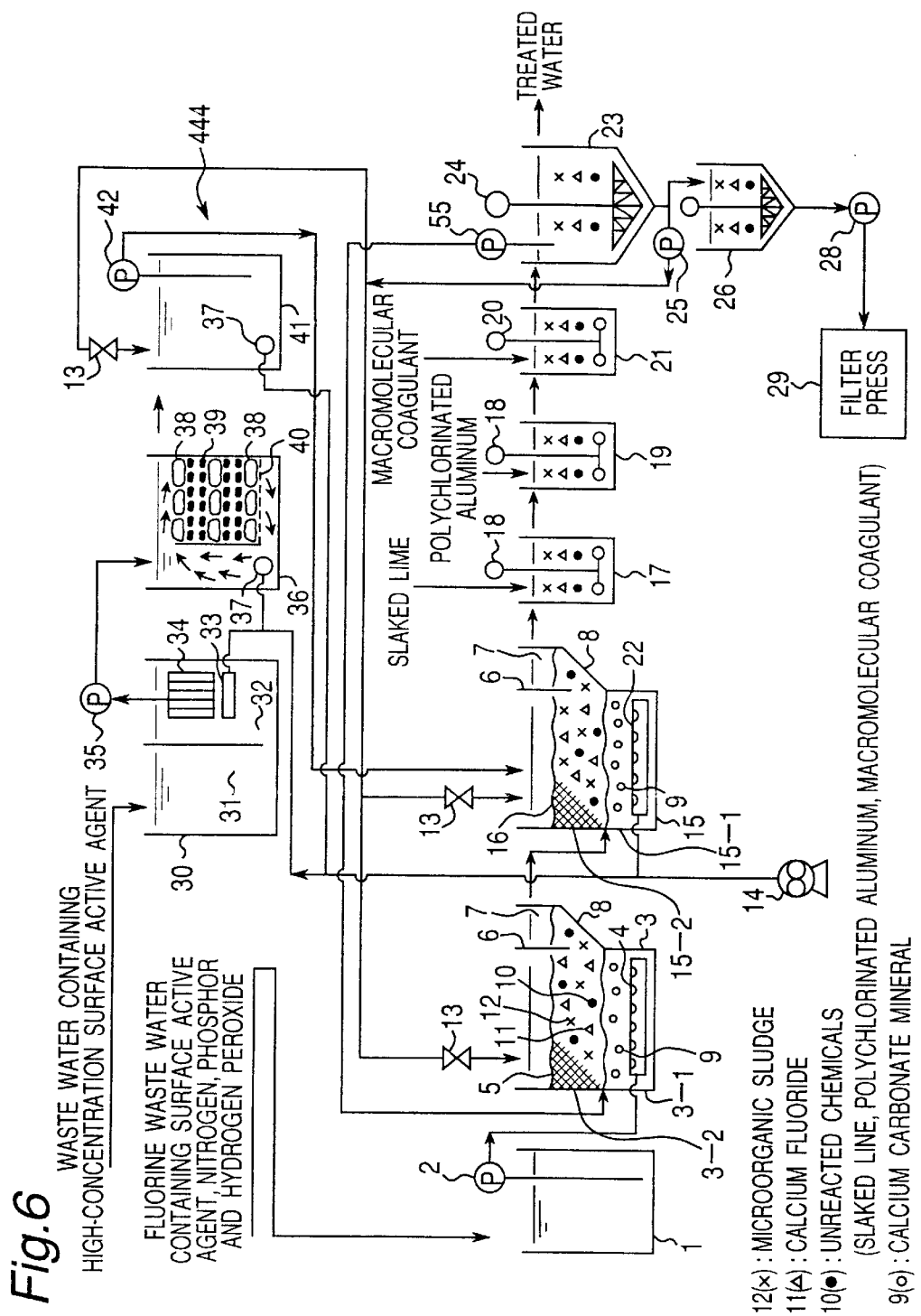
FIG. 6 is a schematic view showing the fifth embodiment of the waste water treatment equipment of the present invention.

Next, FIG. 6 shows the waste water treatment equipment of the fifth embodiment of the present invention. The waste water treatment equipment of this fifth embodiment differs from the aforementioned first embodiment only in the following points (1) and (2). Therefore, same reference numerals are given to the same components as those of the first embodiment and no detailed description is provided for them.

(1) The sludge precipitated in the seventh water tank 23 is sent back not only to the second water tank upper portion 3-2 and the third water tank upper portion 15-2 but also to the eleventh water tank 41 by the sludge return pump 25.

(2) A circulation use air diffusion pipe 37 is placed in the lower portion of the eleventh water tank 41 so as to internally aerate and stir the tank, maintaining the aerobic property for the propagation and culturing of the aerobic microorganism together with the return sludge.

In this fifth embodiment, the sludge precipitated in the seventh water tank (sedimentation tank) 23 is sent back to the aerobic eleventh water tank 41 and mixed with the treated water from the tenth water tank 36. Therefore, the microorganism that can biologically decompose the slightly-soluble surface active agent and has propagated and been cultured in the tenth water tank 36 can be propagated and fixed in the sludge. Then, the sludge water that has been able to be controlled in the eleventh water tank 41 is introduced into the third water tank upper portion 15-2 that is the aerobic tank, and therefore, the various surface active agents (including slightly-soluble ones) in the waste water can be treated by the aerobic microorganism.

In contrast to the fact that the eleventh water tank 41 has the anaerobic state in the aforementioned fourth embodiment of FIG. 5, the eleventh water tank 41 is in an aerobic state according to this fifth embodiment. In general, it has been discovered through experiments that the aerobic microorganism has a superior biodegradability than the anaerobic microorganism. Therefore, if the fourth embodiment and the fifth embodiment are strictly compared with each other, then the fifth embodiment is superior with regard to the surface active agent treatment.

<Sixth Embodiment>

Next, FIG. 7 shows the waste water treatment equipment of the sixth embodiment of the present invention. The waste water treatment equipment of this sixth embodiment differs from the aforementioned first embodiment only in the following points (1), (2), (3) and (4). Therefore, same reference numerals are given to the same components as those of the first embodiment and no detailed description is provided for them.

(1) A twelfth water tank 44, a pump pit 45, a biotic activated carbon tower 47 and a treatment water tank 49 are provided in the stages subsequent to the seventh water tank 23, and the supernatant liquid obtained in the seventh water tank 23 is further highly treated.

(2) The twelfth water tank 44 is filled with activated carbon bags 38 and Bincho charcoal pieces 39 and provided with the circulation use air diffusion pipe 37 that serves as an aerating means.

(3) The treated water in the treatment water tank 49 is conveyed to a blower chamber 50 by a sampling pump 48 and then introduced into a first biotic monitoring water tank 51 and a second biotic monitoring water tank 52 provided inside the blower chamber 50.

(4) The rate of air discharged from the blower 14 is inverter-controlled by way of a signal line 54 by a TOC meter 53 provided inside the second biotic monitoring water tank 52.

In this sixth embodiment, the supernatant liquid obtained in the seventh water tank 23 is further introduced into the twelfth water tank 44, the pump pit 45 and the biotic activated carbon tower 47, allowing the surface active agent in the waste water to be highly treated.

In particular, a very small amount of surface active agent that serves as an organic matter in the waste water is firstly physically adsorbed by the activated carbon inside the activated carbon bags 38 and the Bincho charcoal pieces 39 in the twelfth water tank 44 and thereafter biologically decomposed by the microorganism that is propagated and fixed on the surfaces of the activated carbon inside the activated carbon bag 38 and the Bincho charcoal pieces 39. Accordingly, there is no need for taking the activated carbon inside the activated carbon bags 38 or the Bincho charcoal pieces 39 out of the tank and regenerating the same.

The activated carbon inside the activated carbon bags 38 may be the general granular activated carbon or pellet-shaped activated carbon. The activated carbon is not specifically limited in terms of the type and manufacturer thereof. Specifically, the pellet-shaped activated carbon produced by Kyatara Industries Co., Ltd. may be adopted.

It is to be noted that the activated carbon bag 38 is required to have a construction in which the stored activated carbon and waste water are brought in contact with each other and required to be made of an incorruptible material. In this case, a bag that was made of polypropylene and had a net shape and a capacity of 20 litters was selected for the activated carbon bag 38.

The selected Bincho charcoal piece 39 had a length of about 7 cm and a diameter of about 3 cm to 4 cm. The activated carbon bags 38 and the Bincho charcoal pieces 39 are placed alternately in layers of a thickness of about 40 cm in the twelfth water tank 44. By alternately placing them, gaps (space portions) defined between the activated carbon bags 38 and the Bincho charcoal pieces 39 can be uniformed as far as possible in the tank, allowing the waste water to spread throughout the tank. Then, the waste water uniformly spreads between the gaps by a circulation water flow generated by the air discharged from the circulation use air diffusion pipe 37, by which the filler and the waste water are efficiently brought in contact with each other.

Next, in the twelfth water tank 44, the very small amount of surface active agent in the waste water obtained through the primary advanced treatment flows together with the waste water into the pump pit 45 in an overflow manner and is conveyed to the biotic activated carbon tower 47 by a pump pit pump 46. Then, a very small amount of surface active agent is subjected to physical adsorption treatment (secondary advanced treatment) by the activated carbon in the biotic activated carbon tower 47. Then, the organic matter including the surface active agent adsorbed by the activated carbon is further biologically decomposed by the microorganism propagating on the surface of the activated carbon. Therefore, the activated carbon is in a state in which the activated carbon is practically automatically regenerated, obviating the need for bothering to take the activated carbon out of the tower and regenerate the same. The activated carbon in this state is the biotic activated carbon.

In this sixth embodiment, the twelfth water tank 44 is particularly placed as a pretreatment unit of the biotic activated carbon tower 47. Therefore, the organic matter load on the biotic activated carbon tower 47 is reduced, by which the treatment in the biotic activated carbon tower 47 with respect to the very small amount of surface active agent in the waste water can be made more reliable.

The treated water flowing out of the biotic activated carbon tower 47 flows into the treatment water tank 49. The treatment water tank 49 is provided with a sampling pump 48. This sampling pump 48 conveys the treated water of the treatment water tank 49 to the first biotic monitoring water tank 51 and the second biotic monitoring water tank 52 placed inside the blower chamber 50. The second biotic monitoring water tank 52 is provided with a TOC (Total Organic Carbon) meter, allowing the blower 14 to be inverter-controlled by the TOC concentration of the second biotic monitoring water tank 52. That is, if the TOC concentration of the second biotic monitoring water tank 52 increases, then the rate of air discharged from the blower 14 is increased by the inverter, increasing the rate of air discharged from the circulation use air diffusion pipe 37 provided in the twelfth water tank 44 for the increase in frequency of circulation by the upward flow of air. Thus, by increasing the frequency of the contact of the waste water with the filler inside the twelfth water tank 44 (i.e., the frequency of circulation), the quality of water including TOC in the waste water can be improved.

In this case, a snail is bred as an aquatic living thing in the first biotic monitoring water tank 51, while a guppy is bred as an aquatic living thing in the second biotic monitoring water tank 52. If the room temperature is high and constant throughout the year as in the blower chamber 50, then the water temperatures of the water tanks 51 and 52 are also high and constant. The aquatic living things lay and hatch eggs within a short period of one month to two months, as a consequence of which the influence of the chemical substances of the surface active agent and the like on the alternation of generations can be confirmed. Furthermore, the blower chamber 50 is stable at high environmental temperature throughout the year, and therefore, the treated water evaporates in the monitoring water tanks 51 and 52, consequently allowing the treated water to be condensed. The treated water is thus condensed throughout the year in the monitoring water tanks 51 and 52, and therefore, the influence of the chemical substances of the surface active agent and the like can be confirmed more swiftly than when not condensed.

According to this sixth embodiment, in the case where the waste water has the normal concentration, as shown in FIG. 8A, the retention time of the waste water is made totally not shorter than four hours comprised of the retention time of two hours in the second water tank 3 and the retention time of two hours in the third water tank 15. However, the reaction time in each of the fourth water tank 17, the fifth water tank 19 and the sixth water tank 21 is allowed to be about 20 minutes.

In the case where the waste water has a low concentration, as shown in FIG. 8B, the retention time of the waste water is made totally not shorter than two hours comprised of the retention time of one hour in the second water tank 3 and the retention time of one hour in the third water tank 15. However, the reaction time in each of the fourth water tank 17, the fifth water tank 19 and the sixth water tank 21 is allowed to be about 20 minutes.

<Seventh Embodiment>

Next, FIG. 9 shows the waste water treatment equipment of the seventh embodiment of the present invention. The waste water treatment equipment of this seventh embodiment differs from the aforementioned sixth embodiment of FIG. 7 only in the following points (1), (2) and (3). Therefore, same reference numerals are given to the same components as those of the sixth embodiment and no detailed description is provided for them.

(1) The return of sludge to the third water tank 15 by the sludge return pump 25 of the sedimentation tank in the sixth embodiment is eliminated.

(2) The sludge is sent back to the eleventh water tank 41 by the sludge return pump 25 of the sedimentation tank.

(3) The circulation use air diffusion pipe 37 is provided in the lower portion of the eleventh water tank 41 so as to aerate and stir the inside of the water tank and maintain the aerobic property, propagating and culturing the aerobic microorganism together with the return sludge.

In this seventh embodiment, the sludge precipitated in the seventh water tank (sedimentation tank) 23 is sent back to the aerobic eleventh water tank 41 and mixed with the treated water from the tenth water tank 36. Therefore, the microorganism that can biologically decompose the slightly-soluble surface active agent and has propagated and been cultured in the tenth water tank 36 can be propagated and fixed in the sludge. Then, the sludge water that has been able to be controlled in the eleventh water tank 41 is introduced into the third water tank upper portion 15-2 that is the aerobic tank, and therefore, the various surface active agents (including slightly-soluble ones) in the waste water can be treated by the aerobic microorganism.

<Eighth Embodiment>

Next, FIG. 10 shows the waste water treatment equipment of the eighth embodiment of the present invention. The waste water treatment equipment of this eighth embodiment differs from the aforementioned seventh embodiment of FIG. 9 only in the following point (1). Therefore, same reference numerals are given to the same components as those of the seventh embodiment and no detailed description is provided for them.

(1) Although the calcium carbonate mineral 9 is placed in the second water tank 3 in the seventh embodiment, the no calcium carbonate mineral 9 is placed in the second water tank 3 in this eighth embodiment.

Therefore, in this eighth embodiment, the waste water is treated by the unreacted slaked lime and the unreacted coagulant included in the sludge precipitated in the seventh water tank (sedimentation tank) 23. In this embodiment, the fluorine, phosphor, hydrogen peroxide, nitrogen and surface active agent in the fluorine waste water containing a surface active agent, nitrogen, phosphor and hydrogen peroxide can be treated even when the calcium carbonate mineral 9 is not existing in the second water tank 3. Then, the liquidity of the waste water in the separation chamber 7 of the second water tank 3 can be neutralized.

<Ninth Embodiment>

Next, FIG. 11 shows the waste water treatment equipment of the ninth embodiment of the present invention. The waste water treatment equipment of this ninth embodiment differs from the aforementioned eighth embodiment only in the following point (1). Therefore, same reference numerals are given to the same components as those of the eighth embodiment and no detailed description is provided for them.

(1) Although the sludge precipitated in the seventh water tank 23 is not sent back to the first water tank 1 in the eighth embodiment of FIG. 10, the sludge precipitated in the seventh water tank 23 is sent back to the first water tank 1 in this ninth embodiment.

Therefore, in this ninth embodiment, the waste water can be pretreated by the unreacted slaked lime and the unreacted macromolecular coagulant included in the sludge without using new chemicals. That is, in this ninth embodiment, the first water tank 1 is positioned as a chemical reaction tank, and the first water tank 1 through the sixth water tank are made to serve as a reaction tank. Therefore, the retention time in these reaction tanks become long, and this reduces the possibility of the generation of unreacted chemicals (unreacted slaked lime and unreacted coagulant). In the first water tank 1, the unreacted chemicals in the return sludge are reliably utilized by the fluorine waste water containing a surface active agent, nitrogen, phosphor and hydrogen peroxide, which serves as an acid waste water. The calcium fluoride included in the return sludge, which is slightly soluble, is not dissolved in the acid waste water.

<Tenth Embodiment>

Next, FIG. 12 shows the waste water treatment equipment of the tenth embodiment of the present invention. The waste water treatment equipment of this tenth embodiment differs from the aforementioned sixth embodiment of FIG. 7 only in the following points (1), (2) and (3). Therefore, same reference numerals are given to the same components as those of the sixth embodiment and no detailed description is provided for them.

(1) The third water tank 15 of the sixth embodiment (FIG. 7) is divided into an anterior third water tank 15-3 and a posterior third water tank 15-4, each having a capacity being about one half the capacity of the third water tank 15.

(2) A calcium carbonate mineral 9 is placed in the anterior third water tank 15-3, the air diffusion pipe 22 is placed in the lower portion of the water tank, and the return sludge is sent back to the posterior third water tank 15-4 by the sedimentation tank sludge return pump 25.

(3) The anterior third water tank 15-3 and the posterior third water tank 15-4 are arranged in series with each other.

If the amount of air for aeration of the third water tank 15 is increased to an amount greater than the setting value in order to promote the decomposition of the surface active agent in the aforementioned sixth embodiment shown in FIG. 7, then the calcium carbonate mineral 9 inside the third water tank 15 is more intensely flowed and stirred and mixed with the return sludge, and the sludge adheres to the surface of the calcium carbonate mineral 9 to possibly hinder the reaction.

In contrast to this, in the tenth embodiment of FIG. 12, the calcium carbonate mineral 9 is placed only in the anterior third water tank 15-3. For this reason, the sludge scarcely adheres to the calcium carbonate mineral 9 when the amount of air in the front and rear third water tanks 15-3 and 15-4 is increased to promote the decomposition of the surface active agent, not hindering the reaction. Therefore, this tenth embodiment is more effective than the sixth embodiment of FIG. 7 when treating the surface active agent by increasing the amount of air for aeration.

<Eleventh Embodiment>

Figure 13:
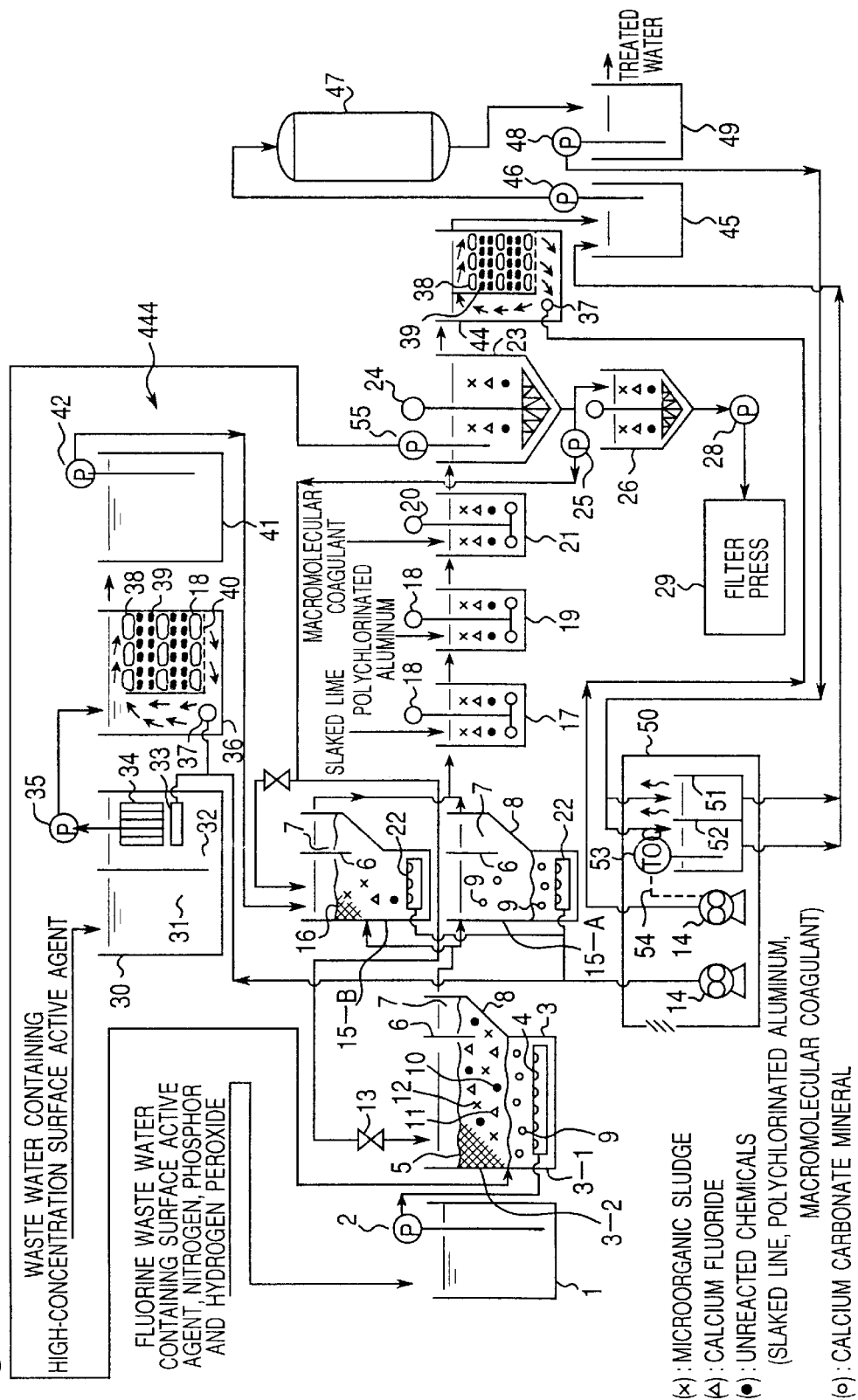
FIG. 13 is a schematic view showing the eleventh embodiment of the waste water treatment equipment of the present invention.

Next, FIG. 13 shows the waste water treatment equipment of the eleventh embodiment of the present invention. The waste water treatment equipment of this eleventh embodiment differs from the aforementioned sixth embodiment of FIG. 7 only in the following points (1), (2) and (3). Therefore, same reference numerals are given to the same components as those of the sixth embodiment and no detailed description is provided for them.

(1) The third water tank 15 of the sixth embodiment of FIG. 7 is divided into a half third water tank 15-A and a half third water tank 15-B, each having a capacity being about one half the capacity of the third water tank 15.

(2) The calcium carbonate mineral 9 is placed in the half third water tank 15-A, the air diffusion pipe 22 is placed in the lower portion of the water tank, and the return sludge is sent back to the half third water tank 15B by the sedimentation tank sludge return pump 25.

(3) The half third water tank 15-A and the half third water tank 15-B are arranged in parallel with each other.

If the amount of air for aeration of the third water tank 15 is increased to an amount greater than the setting value in order to promote the decomposition of the surface active agent in the aforementioned sixth embodiment shown in FIG. 7, then the calcium carbonate mineral 9 inside the third water tank 15 is more intensely flowed and stirred and mixed with the return sludge, and the sludge adheres to the surface of the calcium carbonate mineral 9 to possibly hinder the reaction.

In contrast to this, in this eleventh embodiment, the third water tank 15 is divided into the half third water tank 15-A in which the calcium carbonate mineral 9 is placed and the half third water tank 15-B in which the calcium carbonate mineral 9 is not placed. Accordingly, in this eleventh embodiment, there occurs no such problem that sludge adheres to the surface of the calcium carbonate mineral 9 if the amount of air for aeration is increased. Therefore, this eleventh embodiment is more effective than the sixth embodiment when treating the surface active agent by increasing the amount of air for aeration.

FIRST EXPERIMENTAL EXAMPLE

As a concrete experimental example, a waste water treatment experimental example using the actual treatment equipment having the same structure as that of the first embodiment shown in FIG. 1 will be described next. In this experimental example, the capacity of the first water tank 1 was set to about one cubic meter, the capacity of the second water tank 3 was set to about two cubic meters and the capacity of the third water tank 15 was set to about two cubic meters. The capacity of the fourth water tank 17 was set to about 0.25 cubic meter, the capacity of the fifth water tank 19 was set to about 0.25 cubic meter and the capacity of the sixth water tank 21 was set to about 0.25 cubic meter. The capacity of the seventh water tank 23 was set to about three cubic meters and the capacity of the eighth water tank 26 was set to about one cubic meter.

On the other hand, as a treated water for the waste water containing a high-concentration surface active agent of another system, the treated water was obtained from the water tank equivalent to the eleventh water tank 41 of the actual microorganism treatment equipment 444 of the waste water containing a developing solution and this treated water was introduced into the third water tank upper portion 15-2.

In this experimental equipment, a fluorine waste water containing a surface active agent, nitrogen, phosphor and hydrogen peroxide having pH 2.2, a fluorine concentration of 154 ppm, an anionic surface active agent concentration of 0.12 ppm, a total nitrogen concentration of 14.3 ppm, a phosphor concentration of 11.2 ppm and a hydrogen peroxide concentration of 85 ppm was treated. As a result, the treated waste water had pH 7.4, a fluorine concentration of 6 ppm, an anionic surface active agent concentration of 0.02 ppm, a total nitrogen concentration of 5.3 ppm, a phosphor concentration of 0.3 ppm and a hydrogen peroxide concentration of 1 ppm.

SECOND EXPERIMENTAL EXAMPLE

A second experimental example will be described next. In this second experimental example, the waste water treatment equipment was executed using the experimental equipment having the same structure as that of the sixth embodiment shown in FIG. 7 as concrete experimental equipment. In this experimental example, the capacity of the first water tank 1 was set to about one cubic meter, the capacity of the second water tank 3 was set to about two cubic meters and the capacity of the third water tank 15 was set to about two cubic meters. The capacity of the fourth water tank 17 was set to about 0.25 cubic meter, the capacity of the fifth water tank 19 was set to about 0.25 cubic meter and the capacity of the sixth water tank 21 was set to about 0.25 cubic meter. The capacity of the seventh water tank 23 was set to about three cubic meters and the capacity of the eighth water tank 26 was set to about one cubic meter. The capacity of the biotic activated carbon tower 47 was set to about two cubic meters and the capacity of the treatment water tank 49 was set to about 0.5 cubic meter.

On the other hand, as a treated water for the waste water containing a high-concentration surface active agent of another system, the treated water was obtained from the water tank equivalent to the eleventh water tank 41 of the actual microorganism treatment equipment 444 of the waste water containing a developing solution and this treated water was introduced into the third water tank upper portion 15-2. In this experimental equipment, a fluorine waste water containing a surface active agent, nitrogen, phosphor and hydrogen peroxide having pH 2.4, a fluorine concentration of 157 ppm, an anionic surface active agent concentration of 0.12 ppm, a total nitrogen concentration of 14.7 ppm, a phosphor concentration of 11.0 ppm and a hydrogen peroxide concentration of 88 ppm was treated. As a result, the treated waste water had pH 7.4, a fluorine concentration of 5 ppm, an anionic surface active agent concentration of 0.02 ppm, a total nitrogen concentration of 4.3 ppm, a phosphor concentration of 0.3 ppm and a hydrogen peroxide concentration of 0.5 ppm.

THIRD EXPERIMENTAL EXAMPLE

As a concrete experimental example, a waste water treatment experimental example using the actual treatment equipment having the same structure as that of the third embodiment shown in FIG. 4 will be described next. In this experimental example, the capacity of the first water tank 1 was set to about 300 cubic meters, the capacity of the second water tank 3 was set to about 300 cubic meters and the capacity of the third water tank 15 was set to about 300 cubic meters. The capacity of the fourth water tank 17 was set to about 40 cubic meters, the capacity of the fifth water tank 19 was set to about 40 cubic meters and the capacity of the sixth water tank 21 was set to about 40 cubic meters. The capacity of the seventh water tank 23 was set to about 450 cubic meters and the capacity of the eighth water tank 26 was set to about 100 cubic meters.

On the other hand, as a treated water for the waste water containing a high-concentration surface active agent of another system, the treated water was obtained from the water tank equivalent to the eleventh water tank 41 of the actual microorganism treatment equipment 444 of the waste water containing a developing solution and this treated water was introduced into the third water tank upper portion 15-2.

In this experimental equipment, a fluorine waste water containing a surface active agent, nitrogen, phosphor and hydrogen peroxide having pH 2.4, a fluorine concentration of 164 ppm, an anionic surface active agent concentration of 0.13 ppm, a total nitrogen concentration of 15.3 ppm, a phosphor concentration of 10.2 ppm and a hydrogen peroxide concentration of 78 ppm was treated. As a result, the treated waste water had pH 7.5, a fluorine concentration of 5 ppm, an anionic surface active agent concentration of 0.02 ppm, a total nitrogen concentration of 5.1 ppm, a phosphor concentration of 0.3 ppm and a hydrogen peroxide concentration of 0.5 ppm.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A waste water treatment method for treating a fluorine waste water containing organic matter, nitrogen, phosphor and hydrogen peroxide by introducing the waste water into an anaerobic tank and an aerobic tank, comprising:
   a calcium carbonate mineral placed in the anaerobic tank;
   a biologically treated water of another system introduced into the aerobic tank; and a calcium carbonate mineral placed in the aerobic tank.

2. A waste water treatment method as claimed in claim 1, wherein
   the organic matter is a surface active agent having poor biodegradability.

3. A waste water treatment method as claimed in claim 1, wherein
   the biologically treated water is a treated water obtained by biologically treating a waste water containing a high-concentration surface active agent.

4. A waste water treatment method as claimed in claim 1, wherein
   the biologically treated water is a treated water obtained by biologically treating a waste water containing a developing solution.

5. A waste water treatment method as claimed in claim 1, wherein
   the anaerobic tank has an upper portion constructed of an anaerobic sludge zone and a lower portion constructed of a calcium carbonate mineral zone, and
   the aerobic tank has an upper portion constructed of an aerobic sludge zone and a lower portion constructed of a calcium carbonate mineral zone.

6. A waste water treatment method as claimed in claim 5, wherein
   the anaerobic sludge zone in the upper portion of the anaerobic tank has a sludge that includes an unreacted slaked lime, an unreacted polychlorinated aluminum, an unreacted macromolecular coagulant, a generated calcium fluoride and a microorganism, and
   the aerobic sludge zone in the upper portion of the aerobic tank has a sludge that includes an unreacted slaked lime, an unreacted polychlorinated aluminum, an unreacted macromolecular coagulant, a generated calcium fluoride and a microorganism.

7. A waste water treatment method as claimed in claim 6, wherein
   the sludge is a return sludge from a sedimentation tank of waste water treatment equipment.

8. A waste water treatment method as claimed in claim 6, for treating the waste water firstly in the anaerobic tank and thereafter continuously treating the waste water in the aerobic tank, wherein
   the microorganism in the anaerobic sludge zone of the anaerobic tank is an anaerobic microorganism, and
   the microorganism in the aerobic sludge zone of the aerobic tank is an aerobic microorganism.

* * * * *